(12) United States Patent
Fujisaki et al.

(10) Patent No.: US 11,540,854 B2
(45) Date of Patent: Jan. 3, 2023

(54) ULTRASONIC PROBE, ULTRASONIC TREATMENT INSTRUMENT, AND ULTRASONIC TREATMENT ASSEMBLY

(71) Applicant: Olympus Corporation, Hachioji (JP)

(72) Inventors: Ken Fujisaki, Sagamihara (JP); Takamitsu Sakamoto, Hachioji (JP); Ken Yokoyama, Tachikawa (JP); Yasuyuki Matsumura, Hachioji (JP); Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 237 days.

(21) Appl. No.: 16/713,773

(22) Filed: Dec. 13, 2019

(65) Prior Publication Data
US 2020/0113595 A1   Apr. 16, 2020

Related U.S. Application Data

(63) Continuation of application No. PCT/JP2017/030596, filed on Aug. 25, 2017, which
(Continued)

(51) Int. Cl.
*A61B 17/32* (2006.01)

(52) U.S. Cl.
CPC ............... *A61B 17/320068* (2013.01); *A61B 2017/320073* (2017.08)

(58) Field of Classification Search
CPC ........... A61B 17/320068; A61B 2017/320073; A61B 2017/320072
See application file for complete search history.

(56) References Cited

U.S. PATENT DOCUMENTS 5,989,274 A   11/1999   Davison et al.
6,241,703 B1 *  6/2001   Levin ............... G10K 11/24
                                        606/169
(Continued)

FOREIGN PATENT DOCUMENTS

CN   205964114 U   2/2017
JP   H05-70515 U   9/1993
(Continued)

OTHER PUBLICATIONS

Aug. 29, 2017 International Search Report issued in International Patent Application No. PCT/JP2017/024732.
(Continued)

*Primary Examiner* — Elizabeth Houston
*Assistant Examiner* — Lauren Dubose
(74) *Attorney, Agent, or Firm* — Oliff PLC

(57) ABSTRACT

The disclosed technology is directed to an ultrasonic probe comprises a probe main portion configured to transmit ultrasonic vibration generated by an ultrasonic transducer. A treatment portion is configured on a distal side of the probe main portion along a longitudinal axis thereof. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when being viewed from the treatment portion and one or more surfaces formed into a staircase shape when being viewed from a side opposed to the distal side of the treatment portion. The second direction surfaces further includes a plurality of surfaces formed into a staircase shape toward the distal side.

10 Claims, 13 Drawing Sheets

Related U.S. Application Data is a continuation of application No. PCT/JP2017/026493, filed on Jul. 21, 2017, and a continuation of application No. PCT/JP2017/024734, filed on Jul. 5, 2017, and a continuation of application No. PCT/JP2017/024732, filed on Jul. 5, 2017, and a continuation of application No. PCT/JP2017/024733, filed on Jul. 5, 2017.

(56) References Cited

U.S. PATENT DOCUMENTS

| | | | |
|---|---|---|---|
| 2005/0090829 | A1 | 4/2005 | Martz et al. |
| 2006/0004396 | A1 | 1/2006 | Easley et al. |
| 2006/0253050 | A1 | 11/2006 | Yoshimine et al. |
| 2008/0194999 | A1* | 8/2008 | Yamaha ......... A61B 17/320068 601/2 |
| 2008/0234710 | A1 | 9/2008 | Neurohr et al. |
| 2010/0121197 | A1 | 5/2010 | Ota et al. |
| 2019/0110799 | A1 | 4/2019 | Sun et al. |

FOREIGN PATENT DOCUMENTS

| | | |
|---|---|---|
| JP | H10-005237 | 10/1995 |
| JP | H7-255736 | 1/1998 |
| JP | 2001-502216 A | 2/2001 |
| JP | 2001-079013 | 3/2001 |
| JP | 2010-207431 | 9/2010 |
| JP | 2016-041215 A | 3/2016 |
| WO | 2006/030563 A1 | 3/2006 |
| WO | 2016/205335 A1 | 12/2016 |

OTHER PUBLICATIONS

Aug. 29, 2017 International Search Report issued in International Patent Application No. PCT/JP2017/024733.
Aug. 29, 2017 International Search Report issued in International Patent Application No. PCT/JP2017/024734.
Jan. 7, 2020 Translation of International Preliminary Report on Patentability issued in PCT Patent Application No. PCT/JP2017/024732.
Jan. 7, 2020 Translation of International Preliminary Report on Patentability issued in PCT Patent Application No. PCT/JP2017/024733.
Jan. 7, 2020 Translation of International Preliminary Report on Patentability issued in PCT Patent Application No. PCT/JP2017/024734.
Jan. 7, 2020 Translation of International Preliminary Report on Patentability issued in PCT Patent Application No. PCT/JP2017/030596.
U.S. Appl. No. 16/732,879, filed Jan. 2, 2020 in the name of Fujisaki et al.
U.S. Appl. No. 16/732,873, filed Jan. 2, 2020 in the name of Fujisaki et al.
U.S. Appl. No. 16/732,829, filed Jan. 2, 2020 in the name of Fujisaki et al.
Oct. 10, 2017 International Search Report issued in International Patent Application No. PCT/JP2017/030596.
International Search Report and Written Opinion from corresponding International Application No. PCT/JP2017/030596, dated Aug. 25, 2017.
International Search Report and Written Opinion from corresponding International Application No. PCT/JP2017/024732, dated Jul. 5, 2017.
Nov. 4, 2020 Office Action issued in Japanese Patent Application No. 2019-528271.
Nov. 2, 2021 Office Action issued in Japanese Patent Application No. 2020-195401.
Nov. 9, 2021 Office Action Issued in U.S. Appl. No. 16/732,829.
May 25, 2022 Office Action issued in Chinese Patent Application No. 201780092912.8.
Jul. 21, 2022 Office Action issued In U.S. Appl. No. 16/732,879.

\* cited by examiner

ULTRASONIC PROBE, ULTRASONIC TREATMENT INSTRUMENT, AND ULTRASONIC TREATMENT ASSEMBLY

CROSS-REFERENCE TO RELATED APPLICATION

This application is a continuation application of PCT Application No. PCT/JP2017/030596 filed on Aug. 25, 2017, which in turn claim priority to the PCT Application No. PCT/JP2017/024732 filed on Jul. 5, 2017 in Japan which is hereby incorporated by reference in its entirety.

TECHNICAL FIELD

The disclosed technology relates to an ultrasonic probe, an ultrasonic treatment instrument, and an ultrasonic treatment assembly.

DESCRIPTION OF THE RELATED ART

For example, in Japanese Patent Laid-Open No. 2010-207431, a cutting chip having a treatment portion is disclosed. This cutting chip has a large number of recessed portions and a large number of projected portions in a blade. This cutting chip can appropriately carry out a cutting treatment of a treatment target by using a combination of any recessed portion and projected portion when the treatment portion is moved in various directions.

With the recessed portion of the cutting chip of Japanese Patent Laid-Open No. 2010-207431, the amount of cutting is small compared with the projected portion. Therefore, in a cut area for which a cutting treatment has been carried out by this cutting chip, roughness, that is, steps, i.e., project-shaped parts and recess-shaped parts, are possibly formed. For this reason, for example, an articular surface of a bone including the cut area involves the possibility of the occurrence of a trouble in the articular surface, such as a trouble that an articular surface of an opposed bone gets caught on the articular surface when moving.

BRIEF SUMMARY OF EMBODIMENTS

The disclosed technology is directed to an ultrasonic probe comprises a probe main portion configured to transmit ultrasonic vibration generated by an ultrasonic transducer. A treatment portion is configured to be disposed on a distal side of the probe main portion along a longitudinal axis of the probe main portion. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when being viewed from a distal side of the treatment portion along the longitudinal axis and one or more surfaces formed into a staircase shape when being viewed from a side opposed to the distal side of the treatment portion with respect to the longitudinal axis. The second direction surfaces further includes a plurality of surfaces formed into a staircase shape toward the distal side and one or more surfaces formed into a staircase shape toward the side opposed to the distal side when the treatment portion is viewed from a direction orthogonal to the longitudinal axis.

Another aspect of the disclosed technology is directed to an ultrasonic treatment instrument incorporating an ultrasonic probe comprises a probe main portion configured to transmit ultrasonic vibration generated by an ultrasonic transducer. A treatment portion is configured to be disposed on a distal side of the probe main portion along a longitudinal axis of the probe main portion. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when is viewed from a distal side of the treatment portion along the longitudinal axis and one or more surfaces formed into a staircase shape when is viewed from a side opposed to the distal side of the treatment portion with respect to the longitudinal axis. The second direction surfaces further includes a plurality of surfaces formed into a staircase shape toward the distal side and one or more surfaces formed into a staircase shape toward the side opposed to the distal side when the treatment portion is viewed from a direction orthogonal to the longitudinal axis. A cylindrical sheath covers the probe main portion of the ultrasonic probe. A housing supports a proximal portion of the sheath and connects a proximal portion of the probe main portion to the ultrasonic transducer to a state in which the ultrasonic vibration is transmitted to the probe main portion generated by the ultrasonic transducer.

A further aspect of the disclosed technology is directed to an ultrasonic treatment assembly incorporating an ultrasonic probe that comprises a probe main portion configured to transmit ultrasonic vibration generated by an ultrasonic transducer. A treatment portion is configured to be disposed on a distal side of the probe main portion along a longitudinal axis of the probe main portion. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when is viewed from a distal side of the treatment portion along the longitudinal axis and one or more surfaces formed into a staircase shape when is viewed from a side opposed to the distal side of the treatment portion with respect to the longitudinal axis. The second direction surfaces further includes a plurality of surfaces formed into a staircase shape toward the distal side and one or more surfaces formed into a staircase shape toward the side opposed to the distal side when the treatment portion is viewed from a direction orthogonal to the longitudinal axis. A cylindrical sheath covers the probe main portion of the ultrasonic probe. A housing supports a proximal portion of the sheath and connects a proximal portion of the probe main portion to the ultrasonic transducer to a state in which the ultrasonic vibration is transmitted to the probe main portion generated by the ultrasonic transducer. A transducer unit is defined by the ultrasonic transducer that is connected to the proximal portion of the probe main portion along the longitudinal axis and transmits the ultrasonic vibration to a proximal end of the probe main portion of the treatment portion.

Yet, a further aspect of the disclosed technology is directed to a method of operating an ultrasonic probe that includes a treatment portion having first direction surfaces disposed in a staircase manner in a direction intersecting a longitudinal axis, second direction surfaces disposed in a staircase manner in a direction different from the first direction surfaces, and one edge or a plurality of edges formed by the first direction surfaces and the second direction surfaces. The method comprises contacting a treatment target with the treatment portion; applying ultrasonic vibration energy by using the treatment portion while moving the treatment portion along the longitudinal axis of the ultrasonic probe with respect to the treatment target; and cutting the treatment target therethrough by maneuvering the treatment portion along of the longitudinal axis of the ultrasonic probe.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

An object of the disclosed technology is to provide an ultrasonic probe, an ultrasonic treatment instrument, and an ultrasonic treatment assembly that can prevent the occurrence of a trouble that an articular surface of a bone including a cut area gets caught on an articular surface of an opposed bone when the articular surface of the opposed bone moves when a treatment is carried out.

A description will be made hereinafter about modes for carrying out the disclosed technology with reference to the drawings.

First Embodiment

A description will be made about a first embodiment with reference to FIG. 1 to FIG. 9B.

Figure 1:
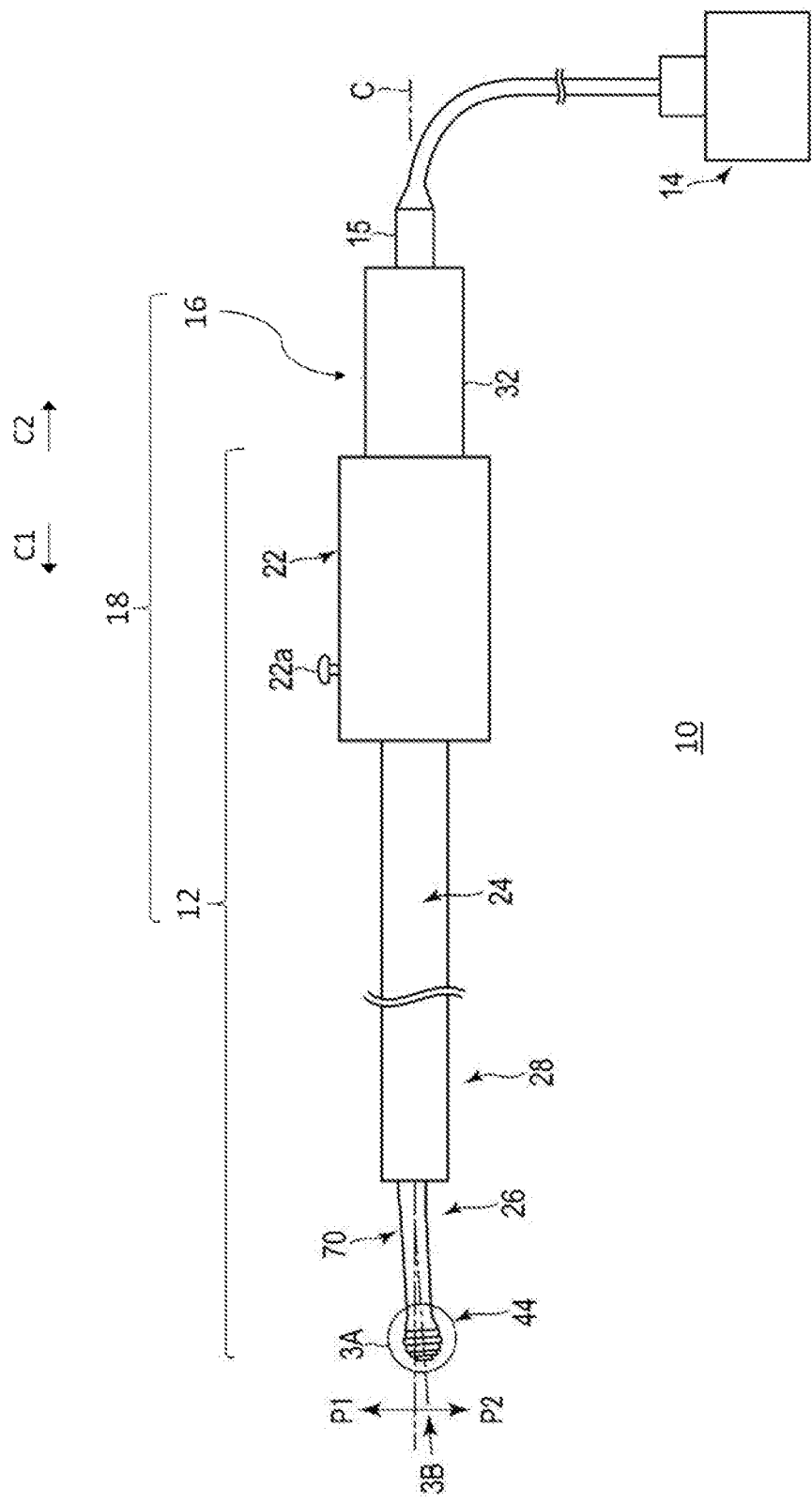
FIG. 1 is a schematic diagram illustrating an ultrasonic treatment system according to a first embodiment.
Figure 2:
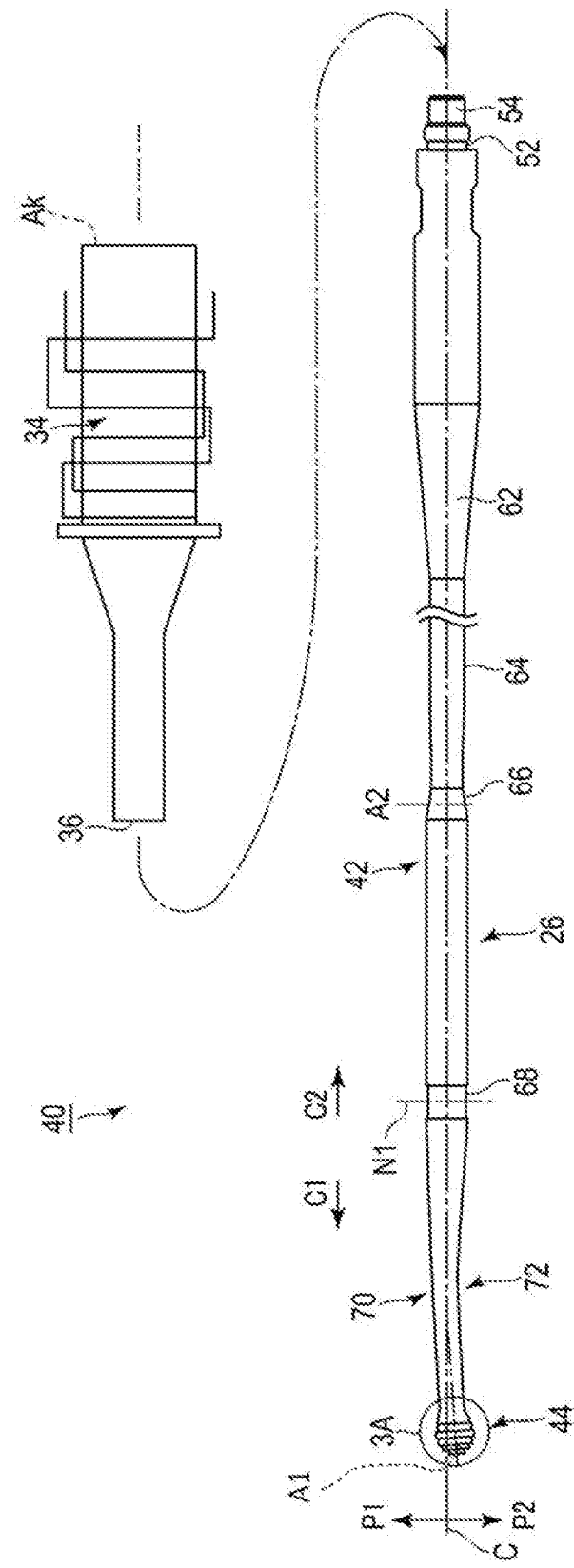
FIG. 2 is a schematic diagram illustrating the configuration of a vibrator unit of an ultrasonic treatment assembly according to the first embodiment.
Figure 3A:
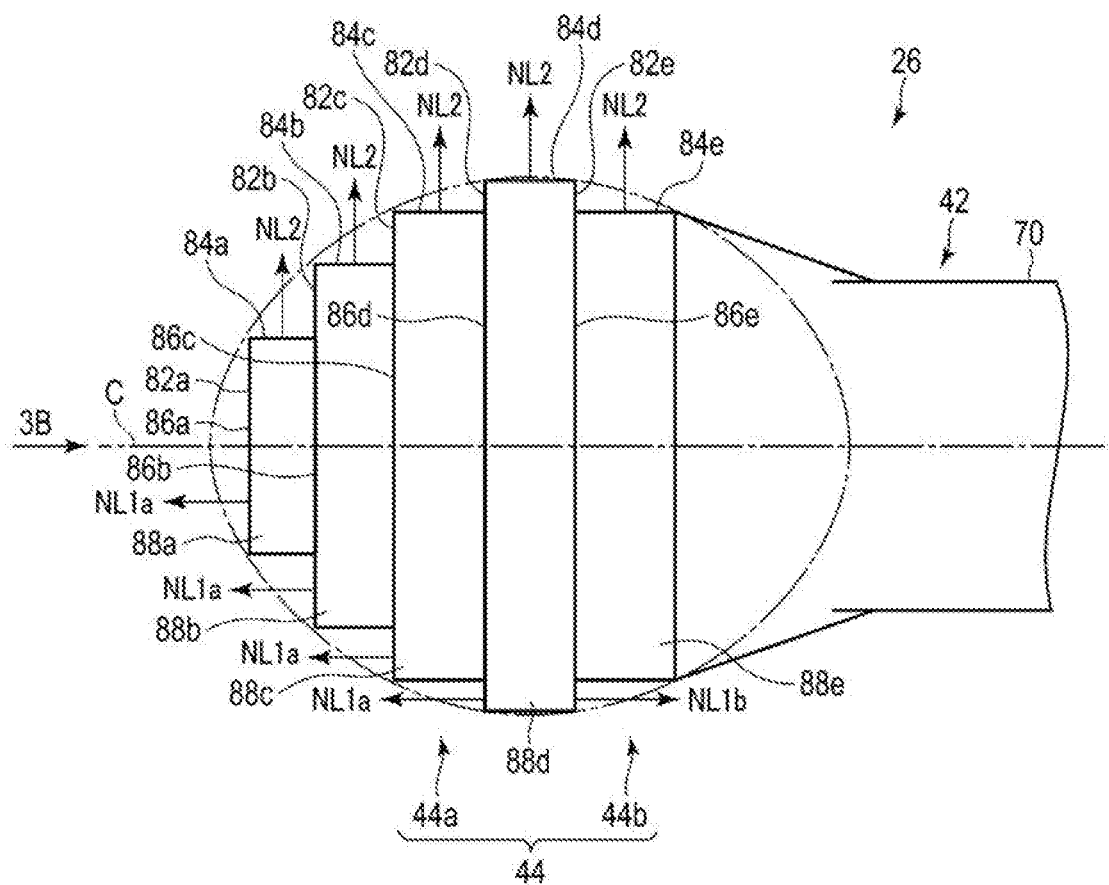
FIG. 3A is a schematic diagram in which a treatment portion and the distal portion of a probe main portion depicted by numeral reference 3A in FIG. 1 and FIG. 2 in the ultrasonic probe according to the first embodiment are enlarged.
Figure 3B:
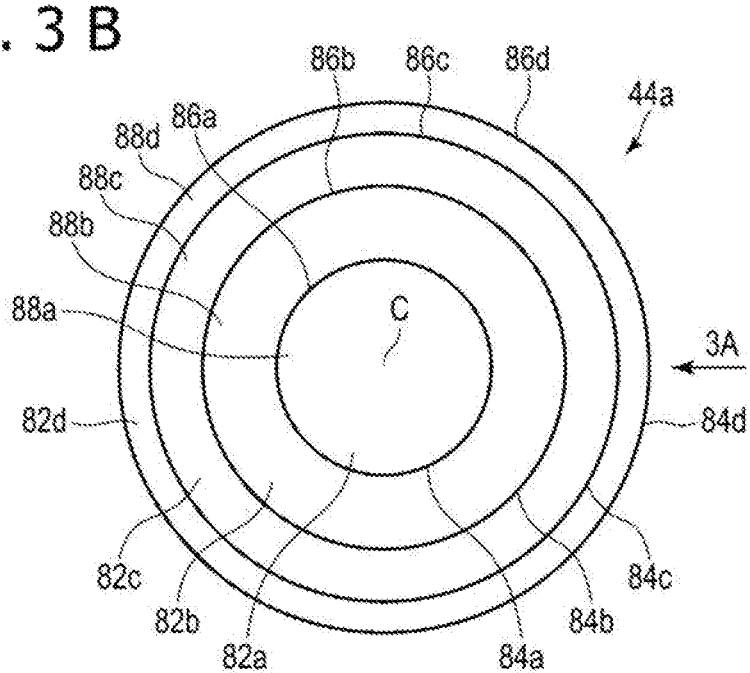
FIG. 3B is a schematic diagram illustrating a distal treatment portion of the treatment portion as viewed from a direction depicted by an arrow 3B in FIG. 1 and FIG. 3A in the ultrasonic probe according to the first embodiment.

FIG. 1 is a diagram illustrating an ultrasonic treatment system 10 of the present embodiment. FIG. 2 is a diagram illustrating an ultrasonic probe 26 and an ultrasonic transducer 34 that will be described hereinafter and configure a vibrator unit 40 to be described hereinafter in a connected state. FIG. 3A is an enlarged view of a treatment portion 44 of the ultrasonic probe 26 and FIG. 3B is a schematic diagram of a distal treatment portion 44a of the treatment portion 44.

As illustrated in FIG. 1, the ultrasonic treatment system 10 has an ultrasonic treatment instrument, i.e., handpiece, 12, an energy control apparatus 14, and a transducer unit 16. The ultrasonic treatment instrument 12 and the transducer unit 16 form an ultrasonic treatment assembly 18.

The ultrasonic treatment instrument 12 has a virtual longitudinal axis C with a substantially straight line shape. Here, one side in the direction along the longitudinal axis C, i.e., longitudinal direction, is the distal side, i.e., side of arrow C1, and the opposite side to the distal side is the proximal side, i.e., side of arrow C2. Furthermore, the ultrasonic treatment instrument 12 is used for an operation of cutting a bone or cartilage in a joint such as an ankle joint, knee joint, elbow joint, wrist joint, or shoulder joint under arthroscopy with an arthroscope 200 illustrated in FIG. 9B.

The ultrasonic treatment instrument 12 has a housing 22 that can be held, a cylindrical sheath 24, and the ultrasonic probe 26. The ultrasonic probe 26 is formed of a material that can favorably transmit ultrasonic vibration generated by the ultrasonic transducer 34 from the proximal end to the distal end along the longitudinal axis C, such as a metal material such as a titanium alloy, for example. The sheath 24 and the ultrasonic probe 26 form an ultrasonic probe unit 28. The housing 22 is extended along the longitudinal axis C and the sheath 24 is joined to the housing 22 from the distal side. Furthermore, the housing 22 supports the proximal portion of the sheath 24 and can connect the proximal portion of a probe main portion 42 to the ultrasonic transducer 34 to the state in which ultrasonic vibration generated by the ultrasonic transducer 34 is transmitted to the probe main portion 42. The sheath 24 is a hollow member that is extended along the longitudinal axis C and has the longitudinal axis C as the center axis or substantially center axis. The ultrasonic probe, i.e., vibration transmitting member, 26 is inserted into the inside of the sheath 24. The sheath 24 supports the outside of the probe main portion 42 of the ultrasonic probe 26. That is, the sheath 24 covers the outside of the probe main portion 42. The distal portion of the ultrasonic probe 26, i.e., vicinity of the distal portion of the probe main portion 42 and the treatment portion 44, protrudes from the distal end of the sheath 24 toward the distal side. Furthermore, to the housing 22, an operation button 22a that is an energy operation input portion operated by an operator is attached.

The transducer unit 16 has an oscillator case 32 and the ultrasonic transducer 34 (see FIG. 2) disposed inside the oscillator case 32. The oscillator case 32 is joined to the housing 22 from the proximal side. Furthermore, inside the housing 22, the ultrasonic transducer 34 is connected to the proximal portion of the probe main portion 42 of the ultrasonic probe 26 from the proximal side. The transducer unit 16 is connected to the energy control apparatus 14 through a cable 15. The energy control apparatus 14 outputs energy to the ultrasonic transducer 34 by detecting input of operation with the operation button 22a. When pressing operation of the operation button 22a is carried out, the energy control apparatus 14 causes ultrasonic vibration to be generated at the ultrasonic transducer 34 by the supply of the energy to the ultrasonic transducer 34. In addition to the operation button 22a or instead of the operation button 22a, a foot switch, i.e., energy operation input portion, that is not illustrated may be connected to the energy control apparatus 14.

Ultrasonic vibration is generated at the ultrasonic transducer 34 by supply of electrical energy, i.e., power, to the ultrasonic transducer 34. Then, the generated ultrasonic vibration is transmitted to the ultrasonic probe 26 and the ultrasonic vibration is transmitted from the proximal side to the distal side in the ultrasonic probe 26. That is, the ultrasonic vibration is input to the proximal end of the probe main portion 42 along the longitudinal axis C and the ultrasonic vibration is transmitted to the treatment portion 44. At this time, the vibrator unit 40 formed by the ultrasonic transducer 34 and the ultrasonic probe 26 vibrates, i.e., longitudinally vibrates, at any frequency in a prescribed frequency range. For example, the vibrator unit 40 is designed to the state in which the vibrator unit 40 carries out the longitudinal vibration at a desired frequency or an appropriate frequency close to the desired frequency by transmitting ultrasonic vibration. In the state in which the vibrator unit 40 illustrated in FIG. 2 longitudinally vibrates at any frequency in the prescribed frequency range, among a vibration antinodes Ai (i=1, 2, . . . , k) of longitudinal vibration transmitted to the ultrasonic probe 26, the most distal vibration antinode A1 is located at the distal end of the ultrasonic probe 26 and the most proximal vibration antinode Ak is located at the proximal end of the ultrasonic transducer 34.

The ultrasonic transducer 34 is extended in such a manner as to have the virtual longitudinal axis C with a substantially straight line shape as the center axis or substantially center axis. An oscillator abutting surface 36 is formed at the tip of the ultrasonic transducer 34. The ultrasonic probe 26 has the probe main portion 42 extended along the longitudinal axis C with the substantially straight line shape and the treatment portion 44 disposed on the distal side of the probe main portion 42 along the longitudinal axis C of the probe main portion 42. Ultrasonic vibration generated by the ultrasonic transducer 34 is transmitted to the probe main portion 42. The treatment portion 44 can cut a treatment target by action of the ultrasonic vibration transmitted through the probe main portion 42. Thus, the treatment portion 44 can form a cut area CA to be described hereinafter.

The probe main portion 42 is extended in such a manner as to have the longitudinal axis C as the center axis or substantially center axis. An abutting surface 52 is formed at the proximal end of the probe main portion 42. Furthermore, in the ultrasonic probe 26, an engagement protrusion 54 that protrudes from the abutting surface 52, i.e., proximal end of the probe main portion 42, toward the proximal side is disposed. The ultrasonic probe 26 is connected to the distal side of the ultrasonic transducer 34 through engagement of the engagement protrusion 54 with an engagement groove (not illustrated) made in the ultrasonic transducer 34 (for example, through screwing of a male screw of the engagement protrusion 54 to a female screw of the engagement groove). That is, to the probe main portion 42, the ultrasonic transducer 34 that generates ultrasonic vibration is connected to the proximal side. In the state in which the ultrasonic probe 26 is connected to the ultrasonic transducer 34, the probe abutting surface 52 of the probe main portion 42 abuts against the oscillator abutting surface 36 of the ultrasonic transducer 34 and the ultrasonic vibration is transmitted from the ultrasonic transducer 34 to the ultrasonic probe 26 through the oscillator abutting surface 36 and the probe abutting surface 52. Thus, the ultrasonic vibration is transmitted to the probe main portion 42 and the ultrasonic vibration is transmitted to the treatment portion 44.

The probe main portion 42 has a horn 62, a sectional area constant portion 64 that is disposed on the distal side relative to the horn 62 and has a constant sectional area, and a sectional area increasing portion 66 disposed on the distal side relative to the sectional area constant portion 64. The probe main portion 42 has also a supported portion 68 disposed on the distal side relative to the sectional area increasing portion 66 and an extended portion 70 disposed on the distal side relative to the supported portion 68.

In the horn 62, the area of the section perpendicular to the longitudinal axis C decreases from the proximal side toward the distal side. In the state in which the vibrator unit 40 longitudinally vibrates at the desired frequency, all vibration antinodes Ai of the longitudinal vibration are located separately from the horn 62. For this reason, in the horn 62, the stress due to the vibration acts and the amplitude of the longitudinal vibration is enlarged.

In the sectional area increasing portion 66, the area of the section perpendicular to the longitudinal axis C increases from the proximal side toward the distal side. In the state in which the vibrator unit 40 longitudinally vibrates at any frequency in the prescribed frequency range, the vibration antinode A2 of the longitudinal vibration is located at the sectional area increasing portion 66. For this reason, in the sectional area increasing portion 66, the stress due to the vibration does not act and the amplitude of the longitudinal vibration hardly decreases. For example, the amplitude of the longitudinal vibration at the vibration antinode A2 located at the sectional area increasing portion 66 is enlarged to several times the amplitude of the longitudinal vibration at the proximal end of the probe main portion 42, i.e., probe abutting surface 52. The vibration antinode A2 is located second closest to the distal side in the vibration antinodes Ai of the longitudinal vibration.

The supported portion 68 is formed into a groove shape that hollows to the inner circumferential side across the whole circumference around the longitudinal axis C. To the outer circumferential surface of the supported portion 68, an elastic member (not illustrated) having electrical insulation and heat resistance is attached. At the supported portion 68, the ultrasonic probe 26 is supported by the inner circumferential surface of the sheath 24 with the intermediary of the elastic member. In the state in which the vibrator unit 40 longitudinally vibrates at the prescribed frequency, a vibration node N1 of the longitudinal vibration is located at the supported portion 68. Here, the vibration node N1 is located closest to the distal side in vibration nodes Nj (j=1, 2, ..., k−1) of the longitudinal vibration. The distal end of the sheath 24 is located on the distal side relative to the supported portion 68. For this reason, the vibration node N1 closest to the distal side is located inside the sheath 24 in the state in which the vibrator unit 40 longitudinally vibrates at the prescribed frequency.

FIG. 1 and FIG. 2 prescribe a first intersecting direction, i.e., direction of an arrow P1, that is certain one direction that intersects, i.e., is substantially perpendicular to, the longitudinal axis C and a second intersecting direction, i.e., direction of an arrow P2, opposite to the first intersecting direction, i.e., first perpendicular direction.

FIG. 3A is a diagram when the distal portion of the ultrasonic probe 26 is viewed from one side in the width direction orthogonal to the first intersecting direction, i.e., direction of the arrow P1, and the second intersecting direction, i.e., direction of the arrow P2. FIG. 3B is a diagram when the treatment portion 44 of the distal portion of the ultrasonic probe 26 is viewed from a direction depicted by an arrow 3B in FIG. 3A.

As illustrated in FIG. 1 and FIG. 2, the extended portion 70 may be extended from the supported portion 68 toward the distal side in the state of bending toward the side of the second intersecting direction P2 or may be extended straight. That is, the extended portion 70 may have a bending portion 72 illustrated in FIG. 2. If the extended portion 70 has the bending portion 72, transverse vibration, i.e., wrong vibration, of the treatment portion 44 is suppressed by appropriately forming the shape of a position close to the supported portion 68 in the extended portion 70.

The treatment portion 44 with which a cutting treatment of a treatment target is carried out through transmission of ultrasonic vibration is disposed on the distal side of the extended portion 70 of the probe main portion 42. Here, for simplification of explanation, a description will be made based on the premise that the longitudinal axis C of the probe main portion 42 and the longitudinal axis of the treatment portion 44 are straight with respect to each other, that is, the treatment portion 44 does not bend with respect to the longitudinal axis C of the probe main portion 42.

As illustrated in FIG. 3A and FIG. 3B, the treatment portion 44 has plural first direction surfaces 82 oriented toward the distal side or the proximal side along the longitudinal axis C and plural second direction surfaces 84 oriented toward a different direction from the first direction surfaces 82. In the present embodiment, the first direction surfaces 82 and the second direction surfaces 84 are orthogonal.

The first direction surfaces 82 are formed as flat surfaces orthogonal to the longitudinal axis C in the present embodiment. For the first direction surfaces 82, normal lines NL1 oriented toward the distal side or the vicinity thereof along the longitudinal axis C and toward the proximal side or the vicinity thereof along the longitudinal axis C are prescribed.

The outer shapes of the first direction surfaces 82 are formed into circular shapes in the present embodiment. The outer shapes of the first direction surfaces 82 can be formed into various shapes such as elliptical shapes and pentagon shapes that are not illustrated.

Some roughness may exist in the first direction surface 82 as long as the vicinity of the outer rim, i.e., edge 86, to be described hereinafter is formed into a flat surface.

The second direction surfaces 84 are formed as surfaces parallel to the longitudinal axis C in the present embodiment. The second direction surfaces 84 have circular ring shapes or are formed into ring shapes through combining plural flat surfaces depending on the outer shapes of the first direction surfaces 82. In the present embodiment, the second direction surfaces 84 are oriented in the direction orthogonal to the longitudinal axis C or a direction close to the orthogonal direction. For this reason, for the second direction surfaces 84, normal lines N2 that are orthogonal or substantially orthogonal to the longitudinal axis C and are oriented in such a direction as to get further away from the longitudinal axis C are prescribed. It suffices that the normal lines NL2 of the second direction surfaces 84 are oriented in a different direction from the normal lines NL1 of the first direction surfaces 82.

In the present embodiment, for simplification of explanation, a description will be made based on the premise that the first direction surfaces 82 are flat surfaces with circular shapes and the second direction surfaces 84 are curved surfaces with circular column shapes.

In the present embodiment, the treatment portion 44 is formed into a staircase shape having plural steps along the longitudinal axis C due to the plural first direction surfaces 82 and the plural second direction surfaces 84. The first direction surfaces 82 have first to fifth axis intersecting surfaces 82a, 82b, 82c, 82d, and 82e shifted from each other about the direction along the longitudinal axis C from the distal side toward the proximal side along the longitudinal axis C. The second direction surfaces 84 have first to fifth axis direction surfaces 84a, 84b, 84c, 84d, and 84e shifted from each other about the direction along the longitudinal axis C from the distal side toward the proximal side along the longitudinal axis C. Furthermore, the plural first direction surfaces 82 and the plural second direction surfaces 84 form cut parts, i.e., edges 86, that can contribute to cutting of a treatment target. The edges 86 have first to fifth edges 86a, 86b, 86c, 86d, and 86e from the distal side toward the proximal side along the longitudinal axis C.

The first axis intersecting surface 82a of the first direction surface 82 is adjacent to the first axis direction surface 84a of the second direction surface 84 on the proximal side along the longitudinal axis C and forms the first edge 86a between the first axis intersecting surface 82a and the first axis direction surface 84a. The second axis intersecting surface 82b of the first direction surface 82 is adjacent to the second axis direction surface 84b of the second direction surface 84 on the proximal side along the longitudinal axis C and forms the second edge 86b between the second axis intersecting surface 82b and the second axis direction surface 84b. The third axis intersecting surface 82c of the first direction surface 82 is adjacent to the third axis direction surface 84c of the second direction surface 84 on the proximal side along the longitudinal axis C and forms the third edge 86c between the third axis intersecting surface 82c and the third axis direction surface 84c. The fourth axis intersecting surface 82d of the first direction surface 82 is adjacent to the fourth axis direction surface 84d of the second direction surface 84 on the proximal side along the longitudinal axis C and forms the fourth edge 86d between the fourth axis intersecting surface 82d and the fourth axis direction surface 84d. The fifth axis intersecting surface 82e of the first direction surface 82 is adjacent to the fifth axis direction surface 84e of the second direction surface 84 on the proximal side along the longitudinal axis C. Furthermore, the fifth axis intersecting surface 82e of the first direction surface 82 is adjacent to the fourth axis direction surface 84d of the second direction surface 84 on the distal side along the longitudinal axis C and forms the fifth edge 86e between the fifth axis intersecting surface 82e and the fourth axis direction surface 84d.

The first to fifth edges 86a, 86b, 86c, 86d, and 86e of the treatment portion 44 of the present embodiment, that is, the second axis intersecting surface 82b, the third axis intersecting surface 82c, and the fourth axis intersecting surface 82d of the first direction surfaces 82, are disposed concentrically with the longitudinal axis C and are each formed into a ring shape. Thus, the parts that can contribute to cutting of a treatment target are seamlessly continuous at the outer circumference of the treatment portion 44. Moreover, the treatment portion 44 of the present embodiment is formed symmetrically or substantially symmetrically with respect to the longitudinal axis C.

In the treatment portion 44, the distance from the longitudinal axis C to the outer circumferential surface is longer in the second axis direction surface 84b than in the first axis direction surface 84a of the second direction surface 84. Similarly, the distance from the longitudinal axis C to the outer circumferential surface is longer in the third axis direction surface 84c than in the second axis direction surface 84b, and the distance from the longitudinal axis C to the outer circumferential surface is longer in the fourth axis direction surface 84d than in the third axis direction surface 84c. That is, the plural edges, i.e., first to fourth edges 86a, 86b, 86c, and 86d, are made to get further away from the longitudinal axis C as the position of the edge is shifted from the distal side toward the proximal side along the longitudinal axis C. For this reason, normal lines NL1a oriented toward the distal side along the longitudinal axis C are prescribed for the first to fourth axis intersecting surfaces 82a, 82b, 82c, and 82d of the first direction surfaces 82.

On the other hand, the distance from the longitudinal axis C to the outer circumferential surface is shorter in the fifth axis direction surface 84e than in the fourth axis direction surface 84d. For this reason, a normal line NL1b oriented toward the proximal side along the longitudinal axis C is prescribed for the fifth axis intersecting surface 82e of the first direction surface 82.

Thus, the treatment portion 44 of the ultrasonic probe 26 according to the present embodiment has the distal treatment portion 44a having a shape like a shape obtained through stacking of plural plate-shaped portions along the longitudinal axis C in a concentric manner and a proximal treatment portion 44b in the state in which plural plate-shaped portions are stacked along the longitudinal axis C concentrically with the distal treatment portion 44a. The distal treatment portion 44a of the present embodiment has a first plate-shaped portion 88a, a second plate-shaped portion 88b, a third plate-shaped portion 88c, and a fourth plate-shaped portion 88d each having a circular disc shape. The distal treatment portion 44a is extended from the distal end toward the proximal side and the plate-shaped portion forming the distal treatment portion 44a has a larger outer diameter when being closer to the proximal side. The proximal treatment portion 44b shares the fourth plate-shaped portion 88d with the distal treatment portion 44a and has a fifth plate-shaped portion 88e with a circular disc shape. The proximal treatment portion 44b is extended from the proximal end of the distal treatment portion 44a toward the proximal side and the plate-shaped portion forming the proximal treatment portion 44b has a larger outer diameter when being closer to the proximal side.

Even when the first to fourth plate-shaped portions 88a, 88b, 88c, and 88d do not have a circular disc shape and are asymmetric with respect to the longitudinal axis C, employing the following configuration is preferable. Specifically, at least part, i.e., part that can contribute to cutting of a treatment target, of the second axis intersecting surface 82b of the first direction surface 82 of the second plate-shaped portion 88b is exposed from the outer rim of the first plate-shaped portion 88a outward in the radial direction with respect to the longitudinal axis C. Furthermore, at least part of the third axis intersecting surface 82c of the first direction surface 82 of the third plate-shaped portion 88c is exposed from the outer rim of the second plate-shaped portion 88b outward in the radial direction with respect to the longitudinal axis C. Moreover, at least part of the fourth axis intersecting surface 82d of the first direction surface 82 of the fourth plate-shaped portion 88d is exposed from the outer rim of the third plate-shaped portion 88c outward in the radial direction with respect to the longitudinal axis C.

The number of steps formed by the first direction surfaces 82 and the second direction surfaces 84 is appropriately set. In the present embodiment, the surface for which the normal line NL1b oriented toward the proximal side along the longitudinal axis C is prescribed is only the fifth axis intersecting surface 82e of the first direction surface 82. However, plural surfaces may be formed to be oriented toward the proximal side along the longitudinal axis C (see FIG. 10 and FIG. 11). Furthermore, the size of the ultrasonic probe 26, that is, the size of the probe main portion 42 and the treatment portion 44, is decided depending on the treatment part and so forth. In addition, the height of the step along the longitudinal axis C prescribed by the second direction surface 84 is appropriately set depending on the size of the treatment portion 44 and the number of steps, for example.

Moreover, in the present embodiment, the edges, i.e., parts that can contribute to cutting of a treatment target, 86 of the treatment portion 44 are disposed on the outer circumferential surface of a virtual substantially ellipsoidal shape, i.e., virtual three-dimensional object, that is long along the longitudinal axis C or in the vicinity of the inside thereof. Specifically, the first to fifth edges 86a, 86b, 86c, 86d, and 86e are disposed on the outer circumferential surface of the substantially ellipsoidal shape or in the vicinity of the inside thereof. Furthermore, part of one or plural edges in the first to fifth edges 86a, 86b, 86c, 86d, and 86e is used as the part that can contribute to cutting of a treatment target.

Next, operation and effects of the ultrasonic probe 26 and the ultrasonic treatment instrument 12 of the present embodiment will be described.

Here, first, by using FIG. 4A to FIG. 6C, schematic diagrams when a cutting treatment of a bone B that is a treatment target Ap is carried out with keeping of the state in which ultrasonic vibration is transmitted to the ultrasonic probe 26 of the present embodiment are illustrated. For simplification of explanation, suppose that the bone B that is the treatment target Ap has a substantially flat shape.

Figure 7A:
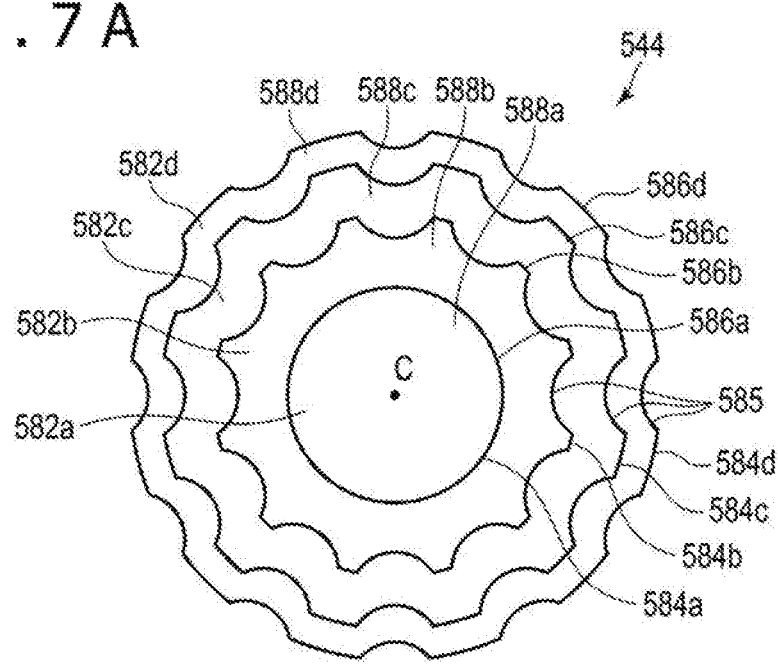
FIG. 7A is a schematic diagram that illustrates a state when a treatment portion of an ultrasonic probe as a comparative example of the first embodiment is viewed from the distal side along the longitudinal axis, and illustrates an example of a non-preferable treatment portion in which recessed grooves that hollow from the circular outer rims of the respective plate-shaped portions of the treatment portion toward the longitudinal axis and are along the longitudinal axis are formed.
Figure 7B:
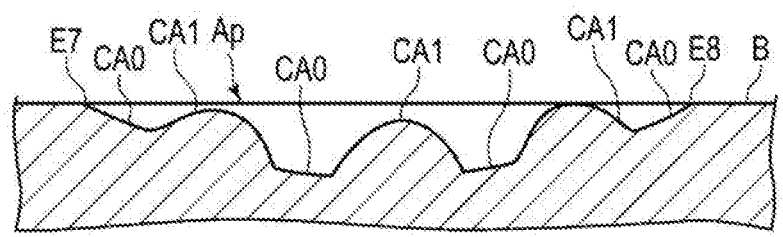
FIG. 7B is a sectional view as viewed from the distal side of the longitudinal axis of a cut area, illustrating the state in which non-preferable project-shaped parts are formed in the cut area when the treatment portion illustrated in FIG. 7A is moved in the same directions as the example illustrated in FIG. 4A.

FIG. 7A illustrates an example of a treatment portion 544 that will be described hereinafter and with which non-preferable project-shaped parts CA1 are formed. FIG. 7B illustrates the cut area CA formed by using the treatment portion 544 illustrated in FIG. 7A.

Figure 8A:
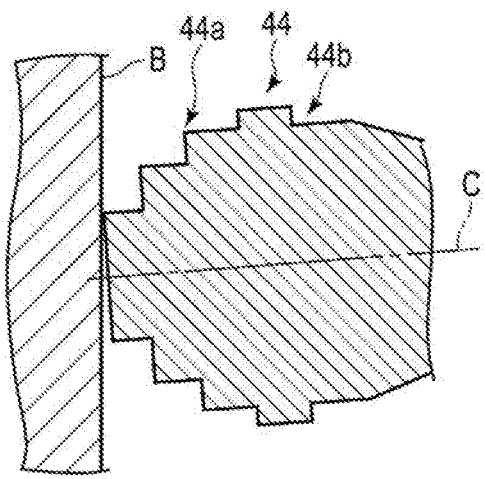
FIG. 8A is a schematic sectional view illustrating the state in which the distal end of the treatment portion is made to abut against a bone in order to form a hole by the treatment portion of the ultrasonic probe according to the first embodiment.
Figure 8B:
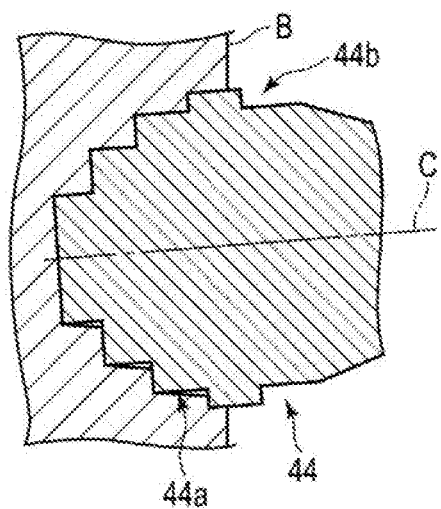
FIG. 8B is a schematic sectional view illustrating the state in which a recessed hole is being formed through one-dimensionally moving the distal end of the treatment portion of the ultrasonic probe according to the first embodiment toward the distal side along a normal line orthogonal to the bone.

FIG. 8A and FIG. 8B illustrate schematic diagrams when a recessed hole H is formed in the bone B that is the treatment target Ap with keeping of the state in which ultrasonic vibration is transmitted to the ultrasonic probe 26 of the present embodiment. For simplification of explanation, suppose that the bone B that is the treatment target Ap has a substantially flat shape.

Figure 4A:
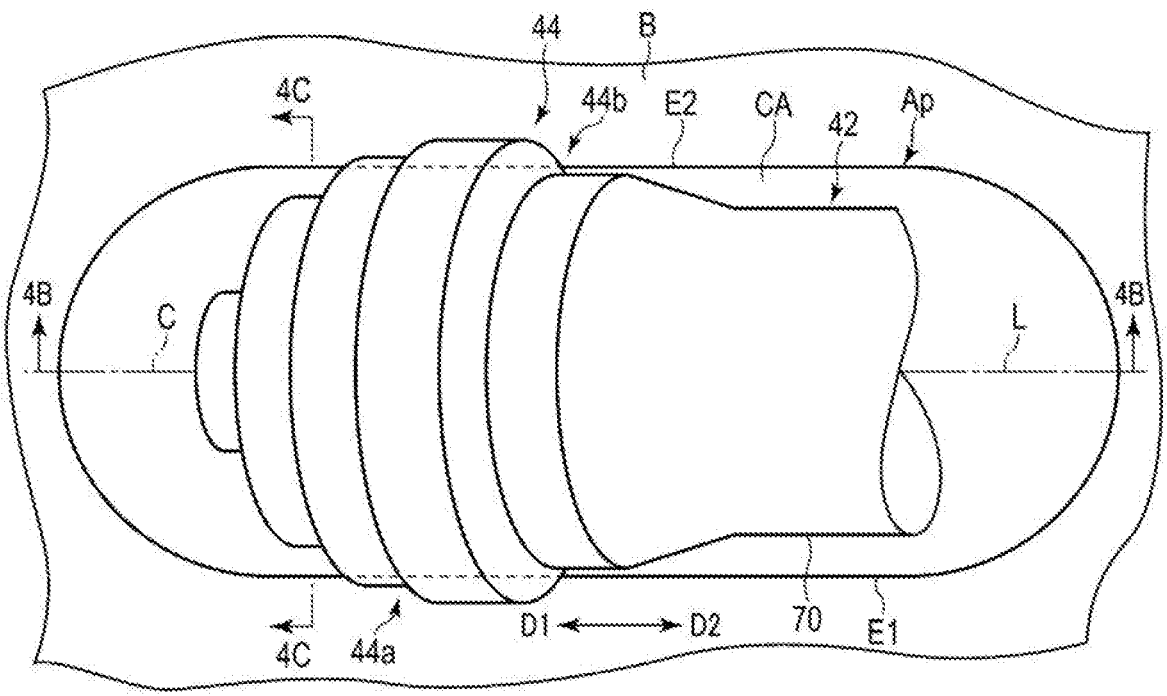
FIG. 4A is a schematic outline diagram illustrating the state in which a cut area is being formed by part of the distal treatment portion through moving the longitudinal axis of the ultrasonic probe in a virtual two-dimensional plane in the state in which part of the distal treatment portion of the ultrasonic probe according to the first embodiment is brought into contact with a bone of a treatment target.
Figure 4B:
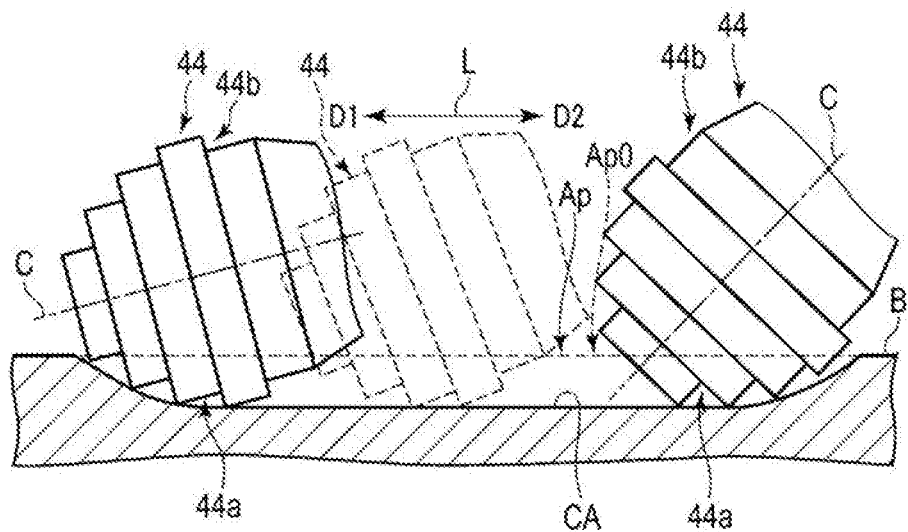
FIG. 4B is a schematic outline diagram that illustrates a section along the longitudinal axis of the cut area along a line 4B-4B in FIG. 4A and illustrates motion of the treatment portion relative to the cut area.
Figure 4C:
FIG. 4C is a schematic sectional view of the cut area along a line 4C-4C in FIG. 4A.

FIG. 4A to FIG. 4C illustrate schematic diagrams when a cutting treatment of a bone that is the treatment target Ap is carried out by using the ultrasonic probe 26 of the present embodiment. Here, an example is illustrated in which a cutting treatment, i.e., removal treatment, of a bone or cartilage is carried out by appropriate one or plural edges in the first to fourth edges 86a, 86b, 86c, and 86d of the distal treatment portion 44a of the treatment portion 44 in a liquid such as saline that is not illustrated.

An operator carries out operation input of pressing operation or the like with the operation button 22a or a foot switch that is not illustrated, for example. Thereby, ultrasonic vibration is generated at the ultrasonic transducer 34 illustrated in FIG. 2 and the generated ultrasonic vibration is transmitted from the proximal side to the distal side in the vibrator unit 40. In the state of transmitting the ultrasonic vibration, the vibrator unit 40 carries out longitudinal vibration in which the vibration direction is substantially parallel to the longitudinal axis C. The treatment portion 44 longitudinally vibrates along the longitudinal axis C in the state in which the treatment portion 44 is in contact with the treatment target Ap, and thereby the treatment target, i.e., bone or cartilage, is cut.

The operator brings one or plural edges in the first to fourth edges 86a, 86b, 86c, and 86d, i.e., even all edges are possible, of the treatment portion 44 into contact with the part desired to be cut in the bone of the treatment target Ap. The operator carries out operation input with the operation button 22a and causes the treatment portion 44 to longitudinally vibrate along the longitudinal axis C. In addition, as illustrated in FIG. 4A, the treatment portion 44 is moved while an appropriate force is applied to the bone of the treatment target Ap.

In the example illustrated in FIG. 4A and FIG. 4B, the treatment portion 44 is moved in a direction, i.e., movement direction, D1 and a direction, i.e., movement direction, D2 that are orthogonal to the first to fourth edges 86a, 86b, 86c, and 86d. The direction D2 is the opposite direction of the direction D1. Furthermore, when the treatment portion 44 is moved in the direction D1 and the direction D2, the cut area CA like one illustrated in FIG. 4C is formed. The cut area CA like one illustrated in FIG. 4C is formed more readily when the treatment portion 44 is moved toward the direction D2 than when the treatment portion 44 is moved toward the direction D1. When the treatment portion 44 is moved as in the example illustrated in FIG. 4A, the tilt of the longitudinal axis, i.e., center axis, C of the treatment portion 44 changes as illustrated in FIG. 4B. For this reason, when the treatment portion 44 is moved toward the direction D1 or toward the direction D2 as in the example illustrated in FIG. 4A, the longitudinal axis C of the ultrasonic probe 26 draws a virtual locus. A virtual two-dimensional plane is formed by the locus drawn due to the movement of the longitudinal axis C of the ultrasonic probe 26 with respect to a longitudinal axis L of the cut area CA at this time. That is, when the treatment portion 44 is moved toward the direction D1 or toward the direction D2, the movement of the longitudinal axis C results in two-dimensional figure, i.e., plane-like, movement. It is preferable that the part that forms the cut area CA in the treatment portion 44 be part of the treatment portion 44 and the remaining part of the treatment portion 44 be in contact with none of other bones and so forth.

As illustrated in FIG. 4B, both when the treatment portion 44 is moved in the direction D1 in the state in which any one or plural, i.e., at least one, edges in the first to fourth edges 86a, 86b, 86c, and 86d are in contact and when the treatment portion 44 is moved in the direction D2 in this state, the bone B of the treatment target Ap is cut due to action of ultrasonic vibration in each case.

In FIG. 4C, a section of the bone B of the treatment target Ap in the width direction orthogonal to the movement direction of the treatment portion 44 is illustrated. That is, FIG. 4C illustrates a section orthogonal to a pair of outer rims E1 and E2 of the cut area CA.

As described hereinbefore, the first to fourth edges 86a, 86b, 86c, and 86d become remoter from the longitudinal axis C from the distal side toward the proximal side along the longitudinal axis C.

For example, the case in which the inclination angle of the longitudinal axis C is smaller with respect to a treatment target Ap0 before cutting, i.e., case in which the angle between the treatment target Ap0 and the longitudinal axis C is close to 0°, is assumed. At this time, for example, in the case of carrying out a treatment with the third edge 86c and the fourth edge 86d of the distal treatment portion 44a along the direction D1, the cutting depth with respect to the treatment target Ap0 before cutting can be made larger in the cutting with the fourth edge 86d immediately after the third edge 86c than in the cutting with the third edge 86c. The part cut with the third edge 86c can be removed by the cutting with the fourth edge 86d. As described hereinbefore, when the inclination angle of the longitudinal axis C is smaller with respect to the treatment target Ap0 before cutting, the final finished surface of the cut area CA in one time of motion in the direction D1 can be formed by the edge closer to the proximal side in the distal treatment portion 44a.

For example, the case in which the inclination angle of the longitudinal axis C is larger with respect to the treatment target Ap0 before cutting, i.e., case in which the angle between the treatment target Ap0 and the longitudinal axis C is close to 90°, is assumed. At this time, for example, in the case of carrying out a treatment by the distal treatment portion 44a along the direction D1, the first edge 86a can contribute to cutting whereas it becomes more difficult for the second edge 86b to contribute to the cutting than the first edge 86a in some cases. As described hereinbefore, when the inclination angle of the longitudinal axis C is larger with respect to the treatment target Ap0 before cutting, the final finished surface of the cut area CA in one time of motion in the direction D1 is formed by the edge closer to the distal side in the distal treatment portion 44a.

Furthermore, if the inclination angle of the longitudinal axis C is an appropriate angle with respect to the treatment target Ap0 before cutting, the final finished surface of the cut area CA in one time of motion in the direction D1 is formed by one edge or plural edges.

By using the ultrasonic probe 26 according to the present embodiment, the section of the cut area CA of the bone of the treatment target Ap is formed as a smooth curved line irrespective of the inclination angle of the longitudinal axis C with respect to the treatment target Ap0 before cutting. That is, the cut area CA of the bone of the treatment target Ap is formed as a smooth curved surface. For this reason, the part that can contribute to cutting of the treatment target Ap, i.e., any one or plural edges in the first to fourth edges 86a, 86b, 86c, and 86d, continuously forms, in the cut area CA, only a recessed surface that hollows relative to the pair of outer rims E1 and E2 of the cut area CA along the movement directions D1 and D2. That is, a project-shaped surface is not formed in the cut area CA.

As described hereinbefore, the smooth cut area CA is formed when the treatment portion 44 of the ultrasonic probe 26 of the present embodiment is used. When the cut area CA is formed as such a smooth curved surface with a recessed shape, a trouble that articular surfaces of bones get caught on each other, and so forth, can be suppressed.

The cutting depth of the cut area CA of the bone B of the treatment target Ap possibly changes depending on the strength of pressing of the treatment portion 44 against the bone B of the treatment target Ap, and so forth. For this reason, the strength of pressing of the treatment portion 44 against the bone B of the treatment target Ap is set high, for example, when the bone B of the treatment target Ap is greatly, i.e., deeply, cut, and the strength of pressing of the treatment portion 44 against the bone B of the treatment target Ap is set low, for example, when the bone B of the treatment target Ap is thinly cut.

Figure 5A:
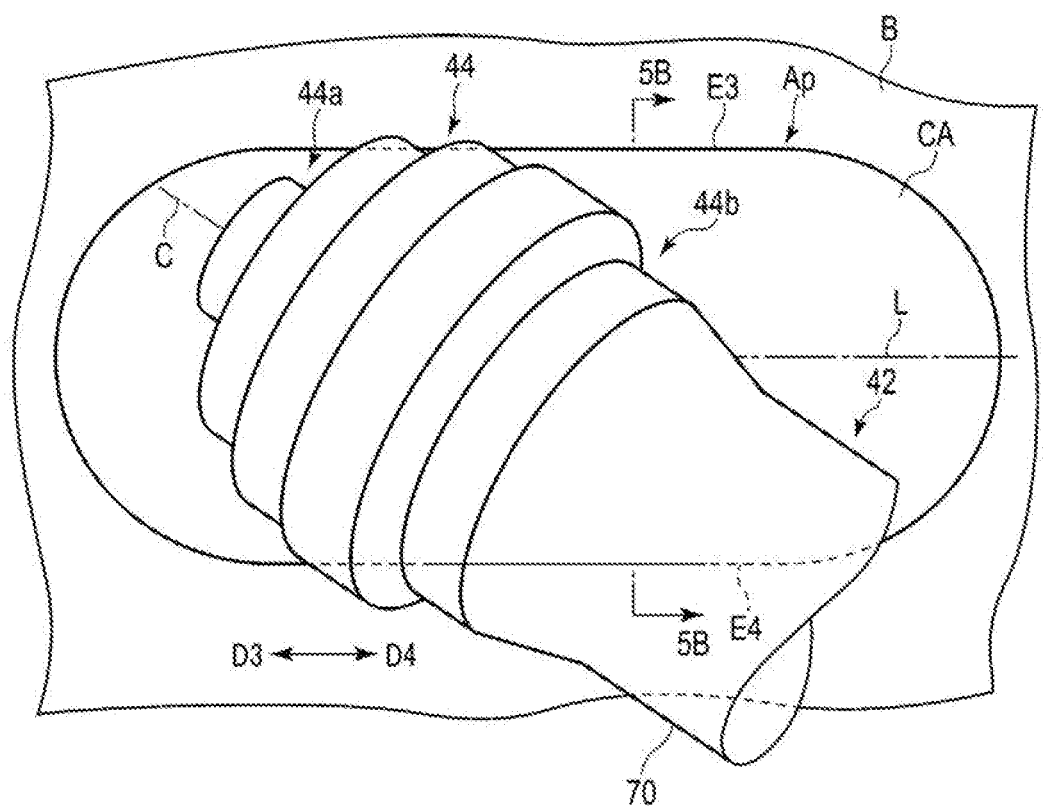
FIG. 5A is a schematic outline diagram illustrating the state in which a cut area is being formed by part of the distal treatment portion through moving the longitudinal axis of the ultrasonic probe in a virtual three-dimensional figure in the state in which part of the distal treatment portion of the ultrasonic probe according to the first embodiment is brought into contact with a bone of a treatment target.
Figure 5B:
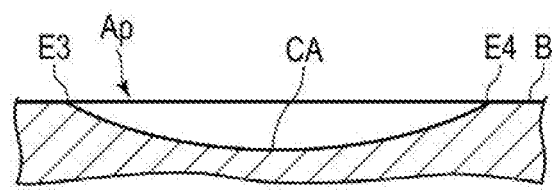
FIG. 5B is a schematic sectional view of the cut area along a line 5B-5B in FIG. 5A.

FIG. 5A and FIG. 5B illustrate schematic diagrams when a cutting treatment of the bone B that is the treatment target Ap is carried out by using the ultrasonic probe 26 of the present embodiment. Here, an example is illustrated in which a cutting treatment, i.e., removal treatment, of a bone or cartilage is carried out by appropriate one or plural edges in the first to fourth edges 86a, 86b, 86c, and 86d of the treatment portion 44 in a liquid such as saline that is not illustrated, similarly to the example illustrated in FIG. 4A to FIG. 4C.

In the example illustrated in FIG. 5A and FIG. 5B, an example is depicted in which the treatment portion 44 is moved in a direction, i.e., movement direction, D3 and a direction, i.e., movement direction, D4 that are different from the direction D1 and the direction D2 depicted in FIG. 4A. The direction D4 is the opposite direction of the direction D3. The direction D3 and the direction D4 are appropriate directions, i.e., oblique directions, between the directions orthogonal to and parallel to the first to fourth edges 86a, 86b, 86c, and 86d. When the treatment portion 44 is moved toward the direction D3 or toward the direction D4 as in the example illustrated in FIG. 5A, the longitudinal axis C of the ultrasonic probe 26 draws a virtual locus similarly to the example illustrated in FIG. 4A. Differently from the example illustrated in FIG. 4A, due to the movement of the longitudinal axis C of the ultrasonic probe 26 with respect to the longitudinal axis L of the cut area CA, the tilt of the longitudinal axis, i.e., center axis, C of the treatment portion 44 changes and the longitudinal axis C moves in such a direction as to deviate from the virtual two-dimensional plane described hereinbefore. For this reason, when the treatment portion 44 is moved as in the example illustrated in FIG. 5A, a virtual three-dimensional figure can be formed based on the locus drawn by the longitudinal axis C of the ultrasonic probe 26 with respect to the longitudinal axis L of the cut area CA when the longitudinal axis C moves. That is, when the treatment portion 44 is moved toward the direction D3 or toward the direction D4, the movement of the longitudinal axis C results in three-dimensional figure-like movement. It is preferable that the part that forms the cut area CA in the treatment portion 44 be part of the treatment portion 44 and the remaining part of the treatment portion 44 be in contact with none of other bones and so forth. In this case, depending on the remaining part of the treatment portion 44, the occurrence of unintended cutting to the other bones and so forth can be prevented.

Both when the treatment portion 44 is moved in the direction D3 in the state in which any one or plural edges in the first to fourth edges 86a, 86b, 86c, and 86d are in contact and when the treatment portion 44 is moved in the direction D4 in this state, the bone B of the treatment target Ap is cut due to action of ultrasonic vibration in each case.

In FIG. 5B, a section of the bone B of the treatment target Ap in the width direction orthogonal to the movement direction of the treatment portion 44 is illustrated. That is, FIG. 5B illustrates a section orthogonal to a pair of outer rims E3 and E4 of the cut area CA. The cut area CA like one illustrated in FIG. 5B is formed more readily when the treatment portion 44 is moved toward the direction D4 than when the treatment portion 44 is moved toward the direction D3.

The section of the cut area CA of the bone of the treatment target Ap is formed as a smooth curved line. That is, the cut area CA of the bone of the treatment target Ap is formed as a smooth curved surface. For this reason, the part that can contribute to cutting of the treatment target Ap, i.e., any one or plural edges in the first to fourth edges 86a, 86b, 86c, and 86d, continuously forms, in the cut area CA, only a recessed surface that hollows relative to the pair of outer rims E3 and E4 of the cut area CA along the movement directions D3 and D4. That is, a project-shaped surface is not formed in the cut area CA.

As described hereinbefore, the smooth cut area CA is formed when the treatment portion 44 of the ultrasonic probe 26 of the present embodiment is used. When the cut area CA is formed as such a smooth curved surface with a recessed shape, a trouble that articular surfaces of bones get caught on each other, and so forth, can be suppressed.

Figure 6A:
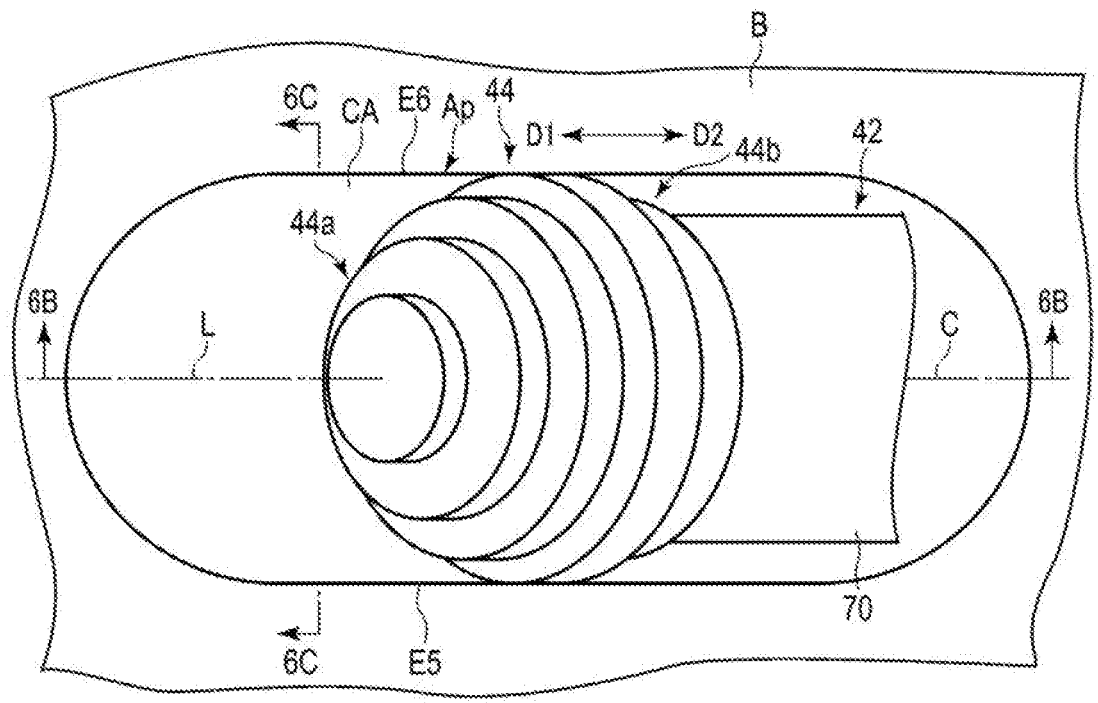
FIG. 6A is a schematic outline diagram illustrating the state in which a cut area is being formed by part of a proximal treatment portion through moving the longitudinal axis of the ultrasonic probe in a virtual two-dimensional plane in the state in which part of the proximal treatment portion of the ultrasonic probe according to the first embodiment is brought into contact with a bone of a treatment target.
Figure 6B:
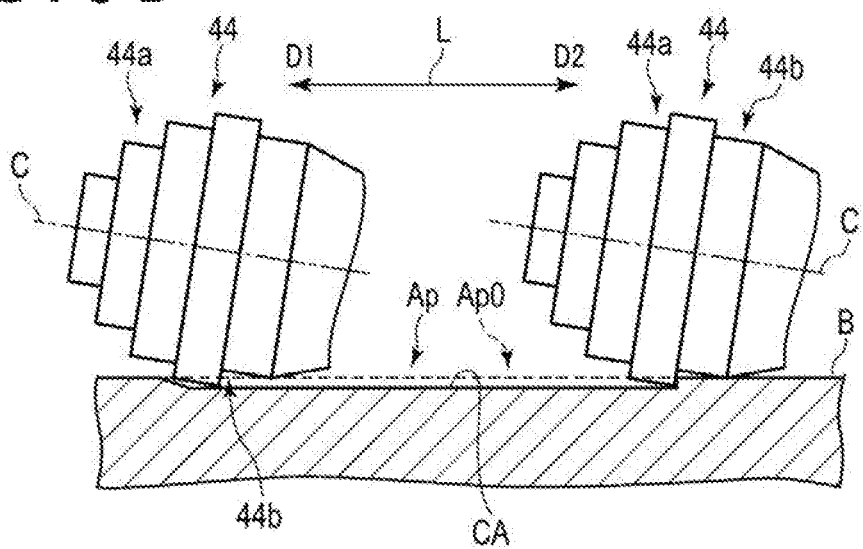
FIG. 6B is a schematic outline diagram that illustrates a section along the longitudinal axis of the cut area along a line 6B-6B in FIG. 6A and illustrates motion of the treatment portion relative to the cut area.
Figure 6C:
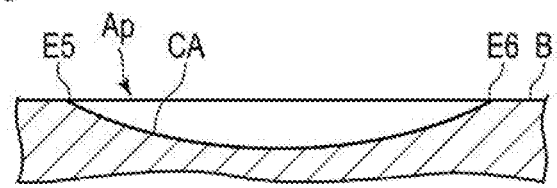
FIG. 6C is a schematic sectional view of the cut area along a line 6C-6C in FIG. 6A.

FIG. 6A to FIG. 6C illustrate schematic diagrams when a cutting treatment of a bone that is the treatment target Ap is carried out by using the ultrasonic probe 26 of the present embodiment. Here, an example is illustrated in which a cutting treatment, i.e., removal treatment, of a bone or cartilage is carried out by the fifth edge 86e of the proximal treatment portion 44b of the treatment portion 44.

As illustrated in FIGS. 6A and 6B, both when the treatment portion 44 is moved in the direction D1 in the state in which the fifth edge 86e is in contact and when the treatment portion 44 is moved in the direction D2 in this state, the bone B of the treatment target Ap is cut due to action of ultrasonic vibration in each case. Although diagrammatic representation is not made, both when the treatment portion 44 is moved in the direction D3 in the state in which the fifth edge 86e is in contact and when the treatment portion 44 is moved in the direction D4 in this state, the bone B of the treatment target Ap is cut due to action of ultrasonic vibration in each case similarly to the description with use of FIG. 5A and FIG. 5B.

In FIG. 6C, a section of the bone B of the treatment target Ap in the width direction orthogonal to the movement direction of the treatment portion 44 is illustrated. That is, FIG. 6C illustrates a section orthogonal to a pair of outer rims E5 and E6 of the cut area CA.

The section of the cut area CA of the bone of the treatment target Ap is formed as a smooth curved line. That is, the cut area CA of the bone of the treatment target Ap is formed as a smooth curved surface. For this reason, the part that can contribute to cutting of the treatment target Ap, i.e., fifth edge 86e, continuously forms, in the cut area CA, only a recessed surface that hollows relative to the pair of outer rims E5 and E6 of the cut area CA along the movement directions D1 and D2. That is, a project-shaped surface is not formed in the cut area CA.

As described hereinbefore, the smooth cut area CA is formed when the treatment portion 44 of the ultrasonic probe 26 of the present embodiment is used. When the cut area CA is formed as such a smooth curved surface with a recessed shape, a trouble that articular surfaces of bones get caught on each other, and so forth, can be suppressed.

As described hereinbefore, with the treatment portion 44 of the ultrasonic probe 26 according to the present embodiment, the section of the cut area CA of the bone of the treatment target Ap is formed as a smooth curved line whichever of the distal treatment portion 44a and the proximal treatment portion 44b is used and is moved in whichever direction, i.e., various directions. For this reason, when the treatment portion 44 of the ultrasonic probe 26 of the present embodiment is used, the cut area CA of a smooth curved surface in which a project-shaped part, i.e., part that protrudes relative to the adjacent part, is formed in the direction orthogonal to the longitudinal axis L of the cut area CA less readily is formed. When the cut area CA of the bone B of the treatment target Ap is formed as such a smooth curved surface with a recessed shape, the articular surface including the cut area CA smoothly moves against an articular surface of another bone in the same joint readily and a trouble that the articular surface including the cut area CA gets caught on an articular surface of another bone, and so forth, can be suppressed.

Therefore, with the treatment portion 44 of the ultrasonic probe 26 according to the present embodiment, the bone B can be shaved and the cut area CA can be formed through moving the treatment portion 44 to the state in which the longitudinal axis C is formed two-dimensionally or three-dimensionally, for example, in the state in which ultrasonic vibration is transmitted. Furthermore, according to the present embodiment, the ultrasonic probe 26 with which an unintended project-shaped part is formed in the cut area CA less readily when a treatment is carried out is provided. Moreover, by using the treatment portion 44 of the ultrasonic probe 26 according to the present embodiment, the cutting treatment of the bone B of the treatment target Ap can be advanced without considering the directionality of the treatment portion 44.

As a comparative example, in FIG. 7A, an example of the treatment portion 544 with which the project-shaped parts CA1 are formed in the cut area CA is illustrated. FIG. 7B illustrates a section in the width direction orthogonal to the movement direction of the treatment portion 544. The treatment portion 544 has plural recessed grooves 585 along the longitudinal axis C in each of respective plate-shaped portions 588b, 588c, and 588d, that is, in each of respective surfaces 582b, 582c, and 582d of first direction surfaces 582, respective surfaces 584b, 584c, and 584d of second direction surfaces 584, and respective edges 586b, 586c, and 586d.

Any one or plural recessed grooves 585 of the treatment portion 544 can contribute to forming the cut area CA through cutting the bone B of the treatment target Ap. Furthermore, for example, when the treatment portion 544 is moved in movement directions with which a virtual plane can be formed by the longitudinal axis, i.e., center axis, L of the cut area CA and the longitudinal axis C of the ultrasonic probe 26, i.e., direction D1 and direction D2 in FIG. 4A and FIG. 4B, smooth curved surfaces CA0 and the project-shaped parts CA1 are possibly formed in the cut area CA by the treatment portion 544 and one or plural recessed grooves 585 formed in the treatment portion 544. The project-shaped parts CA1 are formed between the curved surfaces CA0 continuously.

Thus, when the bone B is cut along the direction D1 and the direction D2 by using the treatment portion 544 illustrated in FIG. 7A of the comparative example, between a pair of outer rims E7 and E8, in addition to the recess-shaped curved surfaces, i.e., recessed surfaces, CA0 that hollow relative to the pair of outer rims E7 and E8, the project-shaped parts CA1 that protrude toward another bone are formed between two curved surfaces CA0, for example. For this reason, it cannot be said that only a recessed surface that hollows relative to the pair of outer rims E7 and E8 is continuously formed in the section of the comparative example illustrated in FIG. 7B.

As described hereinbefore, in the case of carrying out a cutting treatment of the bone B of the treatment target Ap by using the treatment portion 544, depending on the movement direction, it is difficult that the section of the cut area CA be formed as a smooth curved line as a whole and the project-shaped parts CA1 are formed due to the recessed grooves 585 as illustrated in FIG. 7B. Possibly the project-shaped parts CA1 of the cut area CA are continuously formed in the movement direction of the treatment portion 544. For this reason, in the cut area CA, a trouble that the cut area CA gets caught on an articular surface of another bone possibly occurs. Therefore, by using the treatment portion 544, the cut area CA needs to be turned to a smooth curved surface while the project-shaped parts CA1 are removed. However, this work possibly relies on the technical skill of the operator.

On the other hand, the recessed grooves 585 (see FIG. 7A) that hollow toward the opposite side to the side on which the cut area CA is located do not exist at the parts that are brought into contact with the treatment target Ap when the cut area CA is formed in the treatment target Ap and can contribute to cutting of the treatment target Ap, i.e., first to fifth edges 86a, 86b, 86c, 86d, and 86e, in the treatment portion 44 of the probe 26 according to the present embodiment. The term recessed groove 585 here refers to a groove with a substantially U-shape, for example. That is, the recessed groove 585 refers to a groove made through, when certain one bottom surface is defined, forming of a pair of side surfaces that are continuous with the bottom surface and are opposed to each other and opening of a position opposed to the bottom surface. Thus, at the edges 86 of the treatment portion 44 of the probe 26 according to the present embodiment, the recessed grooves 585 (see FIG. 7A) do not exist in the direction from the surface, i.e., cut area CA, actually cut in the state in which the treatment portion 44 is in contact with the bone B of the treatment target Ap toward the longitudinal axis C of the treatment portion 44. Furthermore, the parts that can contribute to cutting of the treatment target Ap, i.e., first to fifth edges 86a, 86b, 86c, 86d, and 86e, in the treatment portion 44 of the probe 26 according to the present embodiment can continuously form only a recessed surface that hollows relative to a pair of outer rims of the cut area CA when being moved in various directions such as movement directions with which the longitudinal axis C can form a virtual plane and/or movement directions with which a virtual three-dimensional FIG. that deviates from a virtual plane can be formed in the state in which ultrasonic vibration is transmitted and in the state in which the treatment portion 44 is in contact with the treatment target Ap in the cut area CA. For this reason, according to the present embodiment, it is possible to provide the ultrasonic probe 26 with which a step such as a project-shaped surface is formed in the cut area CA less readily when a cutting treatment is carried out. Therefore, according to the present embodiment, it is possible to provide the ultrasonic probe 26, the ultrasonic treatment instrument 12, and the ultrasonic treatment assembly 18 that can prevent the occurrence of a trouble that an articular surface of a bone including a cut area gets caught on an articular surface of an opposed bone when the articular surface of the opposed bone moves, and so forth, when a treatment such as a cutting treatment is carried out.

Figure 8C:
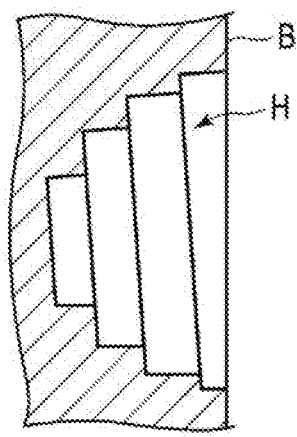
FIG. 8C is a schematic sectional view illustrating the recessed hole formed by using the treatment portion of the ultrasonic probe according to the first embodiment.

FIG. 8A to FIG. 8C illustrate schematic diagrams when a hole, i.e., cut area, H such as a recessed hole or through-hole is formed in the bone B that is the treatment target Ap by using the ultrasonic probe 26 of the present embodiment.

In the case of forming the hole H, an operator carries out operation input with the operation button 22a and moves the ultrasonic probe 26 in a movement direction along the longitudinal axis, i.e., center axis, C, for example, while causing the probe main portion 42 and the treatment portion 44 of the ultrasonic probe 26 to longitudinally vibrate along the longitudinal axis C. Thus, the operator moves the probe main portion 42 and the treatment portion 44 of the ultrasonic probe 26 one-dimensionally along the longitudinal axis C, for example. For this purpose, as illustrated in FIG. 8A, the first axis intersecting surface 82a of the first direction surface 82 of the treatment portion 44 is pressed against the position at which the hole H is desired to be formed on the bone B. Then, for example, as illustrated in FIG. 8B, the ultrasonic probe 26 is moved along the longitudinal axis C to gradually increase the depth of the hole H.

As illustrated in FIG. 8B and FIG. 8C, in the bone B, the recessed hole H is formed into such a shape as to copy the outer shape of the treatment portion 44 or a shape close to it due to action of the ultrasonic vibration transmitted to the ultrasonic probe 26. The recessed hole H is formed as a stepped hole because the treatment portion 44 has the first axis direction surface 84a of the second direction surface 84 parallel to the longitudinal axis C, i.e., first step, between the first axis intersecting surface 82a and the second axis intersecting surface 82b of the first direction surfaces 82. Although diagrammatic representation is not made, when a through-hole is formed, it is formed into the shape of the outer shape of the fourth plate-shaped portion 88d having the largest outer diameter in the treatment portion 44 or a shape close to it.

In FIG. 8A to FIG. 8C, the state in which the longitudinal axis C of the treatment portion 44 deviates from a normal line N of the bone B of the treatment target Ap is illustrated. However, it is also preferable that the longitudinal axis C of the treatment portion 44 correspond with the normal line N of the treatment target Ap.

As described hereinbefore, with the treatment portion 44 of the ultrasonic probe 26 according to the present embodiment, in the state in which ultrasonic vibration is transmitted, the bone B can be shaved and the cut area CA can be formed through moving the treatment portion 44 two-dimensionally or three-dimensionally, for example, and the hole, i.e., cut area, H can be formed through moving the treatment portion 44 one-dimensionally, for example.

In the present embodiment, the example is described in which the normal lines NL1 of the first direction surfaces 82 have both the direction toward the distal side along the longitudinal axis C, i.e., normal line NL1a, and the direction toward the proximal side, i.e., normal line NL1b. A structure in which the normal lines NL1 of the first direction surfaces 82 of the treatment portion 44 are oriented in at least one may be employed. That is, the treatment portion 44 may have both the distal treatment portion 44a and the proximal treatment portion 44b or may have only one.

Figure 9A:
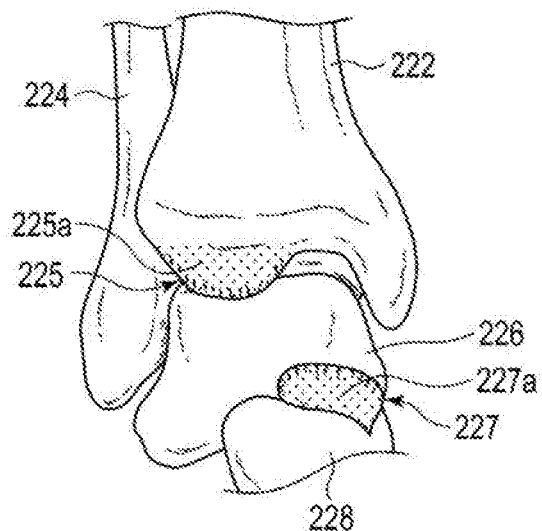
FIG. 9A is a schematic diagram illustrating an ankle joint in which bone spurs are formed.
Figure 9B:
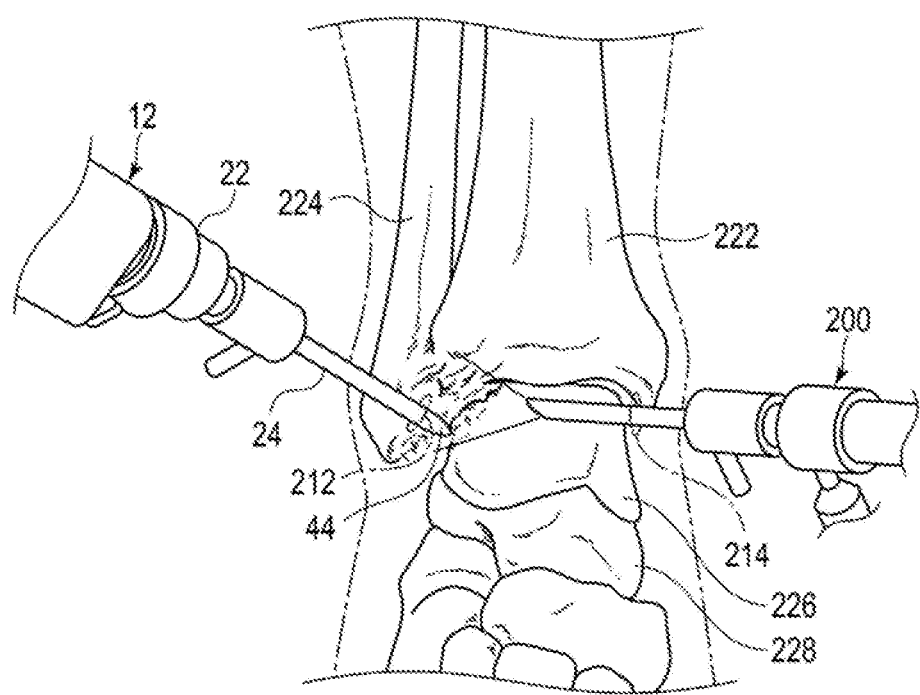
FIG. 9B is a schematic diagram illustrating the state in which the treatment portion of the probe of the ultrasonic treatment system according to the first embodiment and an arthroscope are inserted from portals in a joint cavity of the ankle joint and the bone spur is being excised by the treatment portion while the state of the bone spur is observed by the arthroscope.

Furthermore, as illustrated in FIG. 9A and FIG. 9B, the ultrasonic treatment system 10 according to the present embodiment is used for a treatment of cutting, i.e., removing, part of a bone, cartilage, or the like in a joint such as ankle joint, knee joint, elbow joint, and shoulder joint together with the arthroscope 200. Suppose that the treatment portion 44 of the ultrasonic probe 26 according to the present embodiment is formed to have a size suitable for use for removing, for example, a bone spur in the state in which ultrasonic vibration is transmitted. It is preferable for the ultrasonic probe 26 of the present embodiment to be used for a treatment of a comparatively-small joint such as ankle joint, wrist joint, and elbow joint. However, the ultrasonic probe 26 can be used also for a joint deemed to be wide compared with ankle joint, wrist joint, and elbow joint, such as knee joint and shoulder joint.

In FIG. 9A, the ankle joint of a right foot is illustrated. Numeral reference 222 denotes a tibia. Numeral reference 224 denotes a fibula. Numeral reference 226 denotes a talus. For example, on the outside of the ankle joint, a bone spur 225a is readily generated in a lower-end front surface 225 of the tibia 222. On the inside of the ankle joint, a bone spur 227a is readily generated in a neck 227 of the talus 226.

As illustrated in FIG. 9B, in the case of carrying out a cutting treatment, i.e., removal treatment, of the bone spurs 225a and 227a, portals 212 and 214 are formed on the front outside and the front inside, respectively, that are the front side of the foot. In this example, the distal portion of the ultrasonic probe 26 of the ultrasonic treatment instrument 12 and the distal portion of the sheath 24 are inserted from the portal 212 into the joint cavity of the ankle joint, and the arthroscope 200 is inserted from the portal 214 into the joint cavity of the ankle joint.

While the bone spur 225a of the lower-end front surface 225 of the tibia 222 is observed by using the arthroscope 200, the treatment portion 44 is brought close to or into contact with the bone spur 225a. The operator carries out operation input with the operation button 22a. In the state in which ultrasonic vibration is being transmitted to the bone spur 225a of the lower-end front surface 225 of the tibia 222, the ultrasonic probe 26 is moved in appropriate directions as illustrated in FIG. 4A, FIG. 5A, and FIG. 6A. Thus, the bone spur 225a is gradually shaved by the distal treatment portion 44a and the proximal treatment portion 44b of the treatment portion 44 due to action of the ultrasonic vibration. Similarly, for the bone spur 227a of the neck 227 of the talus 226, the ultrasonic probe 26 is appropriately moved as illustrated in FIG. 4A, FIG. 5A, and FIG. 6A in the state in which ultrasonic vibration is being transmitted. Thus, the bone spur 227a is gradually shaved by the distal treatment portion 44a and the proximal treatment portion 44b of the treatment portion 44 due to action of the ultrasonic vibration. When these bone spurs 225a and 227a are shaved, the operator observes the bone spurs 225a and 227a through the arthroscope 200. This allows the operator to suppress cutting of normal tissue for which excision is unnecessary.

In the joint cavity, cutting the treatment target Ap in a small space is required. For this reason, in the case of carrying out a cutting treatment of the bone spur 225a, the movable range in which the operator can move the treatment portion 44 of the ultrasonic probe 26 is limited to a small range. In the probe 26 in the example illustrated in FIG. 1 and FIG. 2, the distal side is bent toward the side of the second intersecting direction P2 due to the bending portion 72. Thus, when the operator uses part of the edge 86 on the side of the second intersecting direction P2 in the treatment portion 44 in FIG. 1 and FIG. 2, the treatment portion 44 can be allowed to be easily brought into contact with the bone spur 225a and it is easy to suppress contact of the treatment portion 44 with an articular surface and so forth of another bone opposed to the bone spur 225a.

When the bone spur 225a of the lower-end front surface 225 of the tibia 222 is removed, the project-shaped parts CA1 (see FIG. 7B) are formed less readily in the articular surface opposed to the talus 226 in the lower-end front surface 225 of the tibia 222. For this reason, a trouble that articular surfaces get caught on each other when the articular surface of the talus 226 opposed to the articular surface of the lower-end front surface 225 of the tibia 222 is moved, and so forth, are suppressed.

When the bone spur 227a of the neck 227 of the talus 226 is removed, the project-shaped parts CA1 (see FIG. 7B) are formed less readily in the articular surface opposed to an adjacent bone 228 in the neck 227 of the talus 226. For this reason, a trouble that articular surfaces get caught on each other when the articular surface of the adjacent bone 228 opposed to the articular surface of the neck 227 of the talus 226 is moved, and so forth, are suppressed.

Furthermore, in the case of excising the bone spurs 225a and 227a by using the treatment instrument 12 according to the present embodiment, it is possible to excise only the bone spurs 225a and 227a by cutting due to action of ultrasonic vibration. Thus, normal tissue for which excision is unnecessary can be left when the treatment instrument 12 according to the present embodiment is used.

Although diagrammatic representation is omitted, the probe 26 according to the present embodiment can be used for excision of a meniscus in knee osteoarthritis, excision of a bone spur, and so forth, for example. Similarly, the probe 26 according to the present embodiment can be used for excision of a bone spur in osteoarthritis of the elbow or osteoarthritis of the hand and so forth, for example. In addition, by appropriately setting the length, size, and so forth of the probe 26, the probe 26 according to the present embodiment can be used also for an appropriate treatment for the subacromial space of a shoulder joint, for example.

Moreover, the probe 26 according to the present embodiment can be used also in the case of forming a bone hole H in a joint such as ankle joint, knee joint, elbow joint, wrist joint, and shoulder joint.

First Modification Example

Figure 10:
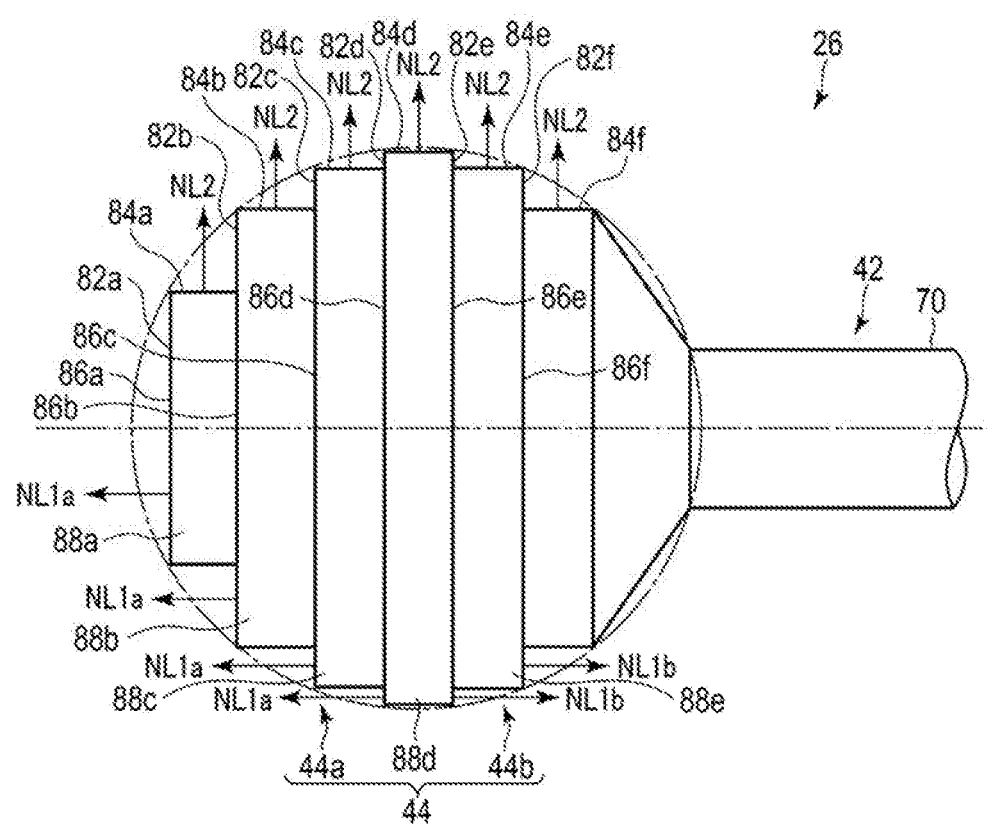
FIG. 10 is a schematic diagram in which a treatment portion of an ultrasonic probe and the distal portion of a probe main portion according to a first modification example of the first embodiment are enlarged.

A description is made about the example in which the outer shape of the treatment portion 44 of the ultrasonic probe 26 illustrated in FIG. 3 is formed into a substantially ellipsoidal shape that is long along the longitudinal axis C. As illustrated in FIG. 10, the outer shape of the treatment portion 44 of the ultrasonic probe 26 may be formed into a substantially spherical shape. At this time, it is preferable that the first to fifth edges 86a, 86b, 86c, 86d, and 86e be disposed on the outer circumferential surface of the substantially spherical shape or in the vicinity of the inside thereof.

In the example illustrated in FIG. 10, the proximal treatment portion 44b has plural, i.e., two, edges 86e and 86f In this example, similarly to the example illustrated in FIG. 3 and FIG. 6A, also in the case of carrying out a cutting treatment of the bone B of the treatment target Ap by using the proximal treatment portion 44b while transmitting ultrasonic vibration, the cut area CA of the bone of the treatment target Ap is formed into a smooth curved surface similarly to the case of carrying out a cutting treatment by the distal treatment portion 44*a*. Furthermore, a project-shaped surface is not formed in the cut area CA due to the use of the treatment portion 44 of the present modification example.

As described hereinbefore, the smooth cut area CA is formed when the treatment portion 44 of the ultrasonic probe 26 of the present modification example is used. When the cut area CA is formed as such a smooth curved surface with a recessed shape, a trouble that articular surfaces of bones get caught on each other, and so forth, can be suppressed.

Second Modification Example

Figure 11:
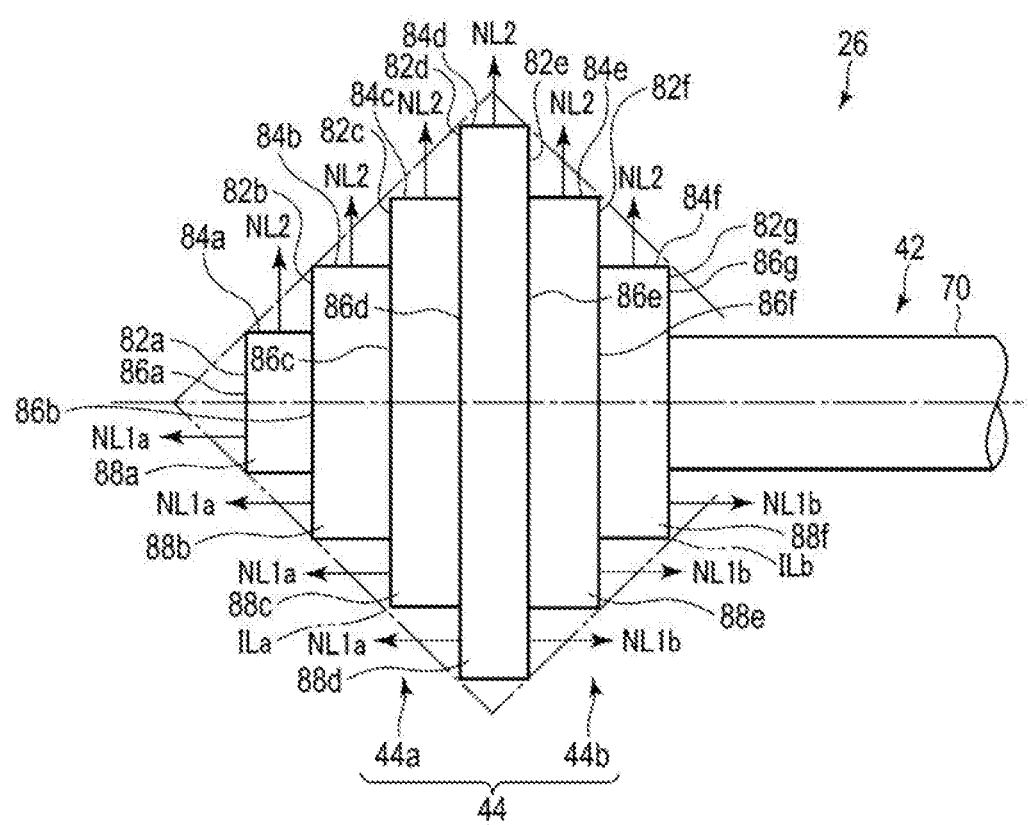
FIG. 11 is a schematic diagram in which a treatment portion of an ultrasonic probe and the distal portion of a probe main portion according to a second modification example of the first embodiment are enlarged.

The first to fifth edges 86*a*, 86*b*, 86*c*, 86*d*, and 86*e* of the treatment portion 44 of the ultrasonic probe 26 do not need to exist on the outer circumferential surface of the substantially ellipsoidal shape (see FIG. 3) or on the outer circumferential surface of the substantially spherical shape (see FIG. 10). As illustrated in FIG. 11, the first to fifth edges 86*a*, 86*b*, 86*c*, 86*d*, and 86*e* of the treatment portion 44 of the ultrasonic probe 26 may exist on linear virtual lines ILa and ILb, for example. Also here, the first to sixth plate-shaped portions 88*a*, 88*b*, 88*c*, 88*d*, 88*e*, and 88*f* are each formed into a substantially circular disc shape and are disposed concentrically around the longitudinal axis C.

Also in the case of using the treatment portion 44 of the probe 26 according to the present modification example, similarly to the case of using the treatment portion 44 illustrated in FIG. 3 and FIG. 10, the cut area CA of the bone of the treatment target Ap is formed into a smooth curved surface in the case of carrying out a cutting treatment of the bone B of the treatment target Ap by using the distal treatment portion 44*a* and/or the proximal treatment portion 44*b* while transmitting ultrasonic vibration. Furthermore, a project-shaped surface is not formed in the cut area CA due to the use of the treatment portion 44 of the present modification example.

As described hereinbefore, the smooth cut area CA is formed when the treatment portion 44 of the ultrasonic probe 26 of the present modification example is used. When the cut area CA is formed as such a smooth curved surface with a recessed shape, a trouble that articular surfaces of bones get caught on each other, and so forth, can be suppressed.

Second Embodiment

Next, a second embodiment will be described by using FIG. 12A to FIG. 12C. The present embodiment is a modification example of the first embodiment including the respective modification examples. The same member and/or a member having the same function as the member described in the first embodiment is given the same numeral reference as much as possible and detailed description thereof is omitted.

Figure 12A:
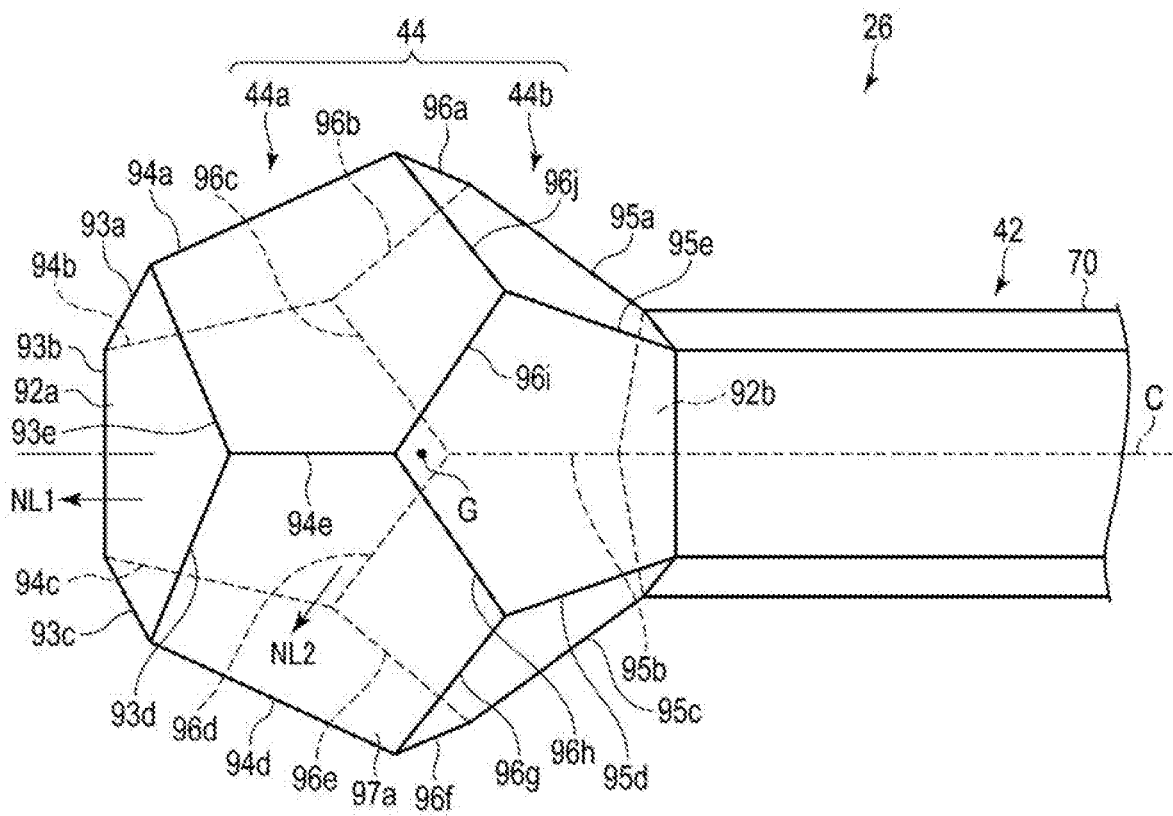
FIG. 12A is a schematic diagram in which a treatment portion of an ultrasonic probe and the distal portion of a probe main portion according to a second embodiment are enlarged.

As illustrated in FIG. 12A, the treatment portion 44 according to the present embodiment does not have the staircase shape described in the first embodiment and is formed through combining plural planes as a polyhedron. The treatment portion 44 according to the present embodiment is formed as a regular dodecahedron, for example. The regular dodecahedron is a projected polyhedron obtained by surrounding a space by twelve pentagons. The treatment portion 44 according to the present embodiment has one pentagonal face as a distal surface 92*a* and has the pentagonal face on the opposite side across the center of gravity G, i.e., center, of the treatment portion 44 as a proximal surface 92*b*. The proximal surface 92*b* of the treatment portion 44 corresponds with the distal end of the probe main portion 42.

Twenty five sides between adjacent faces of the treatment portion 44 are each formed as an edge. The treatment portion 44 has the distal treatment portion 44*a* and the proximal treatment portion 44*b*, with the boundary being ten edges 96*a*, 96*b*, 96*c*, 96*d*, 96*e*, 96*f*, 96*g*, 96*h*, 96*i*, and 96*j* excluding edges 93*a*, 93*b*, 93*c*, 93*d*, and 93*e* of the sides of the pentagon forming the distal surface 92*a*, edges 94*a*, 94*b*, 94*c*, 94*d*, and 94*e* linked to the vertices of the pentagon of the distal surface 92*a*, and edges 95*a*, 95*b*, 95*c*, 95*d*, and 95*e* linked to the vertices of the pentagon of the proximal surface 92*b*. The ten edges 96*a*, 96*b*, 96*c*, 96*d*, 96*e*, 96*f*, 96*g*, 96*h*, 96*i*, and 96*j* can be used as part of the distal treatment portion 44*a* and be used as part of the proximal treatment portion 44*b*.

The parts that can contribute to cutting of the treatment target Ap, i.e., edges 93*a*, 93*b*, 93*c*, 93*d*, and 93*e* of the sides of the pentagon forming the distal surface 92*a* and ten edges 96*a*, 96*b*, 96*c*, 96*d*, 96*e*, 96*f*, 96*g*, 96*h*, 96*i*, and 96*j* forming the boundary between the distal treatment portion 44*a* and the proximal treatment portion 44*b*, are seamlessly continuous in a ring manner.

For example, as the part that can contribute to cutting of the treatment target Ap, one edge 93*d* will be considered as one example. In the case of carrying out a cutting treatment of the treatment target Ap by using the edge 93*d*, the edge 93*d* is formed by the pentagonal face, i.e., first direction surface, 92*a* that is surrounded by the edges 93*a*, 93*b*, 93*c*, 93*d*, and 93*e* and has the normal line NL1 oriented in a direction intersecting the cut area CA and a pentagonal face, i.e., second direction surface, 97*a* that is surrounded by the edges 93*d*, 94*d*, 94*e* 96*g*, and 96*h* and is adjacent to the face, i.e., first direction surface, 92*a* described hereinbefore and has the normal line NL2 oriented in a different direction from the surface 92*a*.

Similarly, also regarding other adjacent faces that share one edge, i.e., side, in the treatment portion 44, when the normal line to one face is oriented in a direction intersecting the cut area, the normal line to the other face is oriented in a different direction from the one face. Furthermore, the one face and the other face are shifted along the longitudinal axis C and form the part that contributes to cutting of the treatment target Ap, i.e., shared edge. In the treatment portion 44 according to the present embodiment, a large number of adjacent faces that share the edge exist.

For this reason, differently from the description in the first embodiment, the normal lines NL1 and NL2 are possibly changed depending on the faces that contribute to the cutting treatment on condition that the faces share one edge.

An operator carries out a cutting treatment through moving the treatment portion 44 in movement directions with which a virtual plane can be formed by the longitudinal axis, i.e., center axis, L of the cut area, i.e., cut surface, CA and the longitudinal axis C of the ultrasonic probe 26 (see FIG. 3A and FIG. 4A), for example. At this time, a virtual two-dimensional plane can be formed based on the locus drawn by the longitudinal axis C of the ultrasonic probe 26 with respect to the longitudinal axis L of the cut area CA when the longitudinal axis C moves. Furthermore, the operator carries out a cutting treatment through moving the treatment portion 44 in movement directions with which a virtual three-dimensional figure can be formed by the longitudinal axis L of the cut area CA and the longitudinal axis C of the ultrasonic probe 26 illustrated in FIG. 5A. At this time, the virtual three-dimensional figure can be formed based on the locus drawn by the longitudinal axis C of the ultrasonic probe 26 with respect to the longitudinal axis L of the cut area CA when the longitudinal axis C moves.

Figure 12B:
FIG. 12B is one example of a sectional view of a cut area formed when the treatment portion illustrated in FIG. 12A is moved in the same direction as the movement direction depicted by numeral reference D2 in FIG. 4A.

FIG. 12B illustrates a section orthogonal to a pair of outer rims Ea and Eb of the cut area CA. FIG. 12C illustrates a section orthogonal to a pair of outer rims Ec and Ed of the cut area CA. The finished surface of the cut area CA in one time of motion is formed by one edge or plural edges.

Figure 12C:
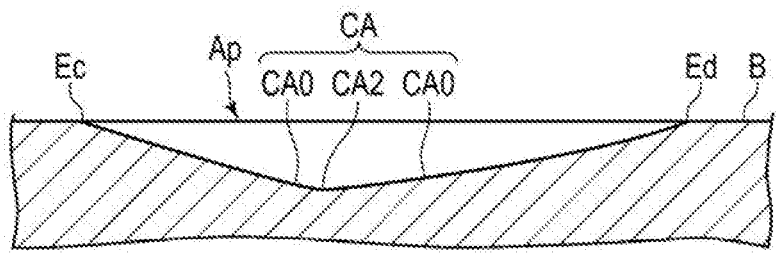
FIG. 12C is one example of a sectional view of a cut area formed when the treatment portion illustrated in FIG. 12A is moved in the same direction as the movement direction depicted by numeral reference D1 in FIG. 4A.

As in the examples illustrated in FIG. 12B and FIG. 12C, by using the ultrasonic probe 26 according to the present embodiment, the cut area CA of the bone of the treatment target Ap is formed as a smooth curved surface.

The cut area CA like one illustrated in FIG. 12B is formed more readily when the treatment portion 44 having the shape illustrated in FIG. 12A in the present embodiment is moved toward the direction D2 illustrated in FIG. 4A than when the treatment portion 44 is moved toward the direction D1. Similarly, the cut area CA like one illustrated in FIG. 12C is formed more readily when the treatment portion 44 is moved toward the direction D1 illustrated in FIG. 4A than when the treatment portion 44 is moved toward the direction D2.

As in the example illustrated in FIG. 12B, for example, depending on the position of the contact surface of the treatment portion 44 to the bone B of the treatment target Ap, the movement direction of the treatment portion 44, and so forth, the section of the cut area CA is formed as a smooth curved line irrespective of the inclination angle of the longitudinal axis C with respect to the treatment target Ap0 before cutting. That is, the cut area CA of the bone of the treatment target Ap is formed as a smooth curved surface. For this reason, the part that can contribute to cutting of the treatment target Ap, i.e., edge, continuously forms, in the cut area CA, only a recessed surface that hollows relative to the pair of outer rims Ea and Eb of the cut area CA along the movement directions D1 and D2. That is, a project-shaped surface is not formed in the cut area CA.

As in the example illustrated in FIG. 12C, for example, depending on the position of the contact surface of the treatment portion 44 to the bone B of the treatment target Ap and the movement direction of the treatment portion 44, a linear part CA2 along the longitudinal axis L of the cut area CA is possibly formed by, for example, one edge (for example, numeral reference 94*e*) of the treatment portion 44. Although the linear part CA2 is possibly formed due to the use of the ultrasonic probe 26 according to the present embodiment as described hereinbefore, the project-shaped part CA1 (see FIG. 7B) that protrudes toward another bone is not formed between two curved surfaces CA0. For this reason, the part that can contribute to cutting of the treatment target Ap, i.e., any one or plural edges in the edges 93*a*, 93*b*, 93*c*, 93*d*, and 93*e* of the sides of the pentagon forming the distal surface 92*a*, the edges 94*a*, 94*b*, 94*c*, 94*d*, and 94*e* linked to the vertices of the pentagon of the distal surface 92*a*, the edges 95*a*, 95*b*, 95*c*, 95*d*, and 95*e* linked to the vertices of the pentagon of the proximal surface 92*b*, and the ten edges 96*a*, 96*b*, 96*c*, 96*d*, 96*e*, 96*f*, 96*g*, 96*h*, 96*i*, and 96*j* described hereinbefore forming the boundary between the distal treatment portion 44*a* and the proximal treatment portion 44*b*, in the treatment portion 44 according to the present embodiment continuously forms, in the cut area CA, only a recessed surface that hollows relative to the pair of outer rims Ec and Ed of the cut area CA along the movement directions D1 and D2. That is, a project-shaped surface is not formed in the cut area CA.

The part that can contribute to cutting of the treatment target Ap, i.e., edge, in the treatment portion 44 according to the present embodiment continuously forms, in the cut area CA, only a recessed surface that hollows relative to the pair of outer rims of the cut area CA along the movement directions D3 and D4 similarly to the case illustrated in FIG. 5B. That is, a project-shaped surface is not formed in the cut area CA.

As described hereinbefore, in the state in which the treatment portion 44 is in contact with the treatment target, the treatment portion 44 forms the cut area CA in the treatment target Ap by movement in movement directions, i.e., D1 and D2, with which the longitudinal axis C can form a virtual plane and/or movement directions, i.e., D3 and D4, with which a virtual three-dimensional figure that deviates from a virtual plane can be formed. On this occasion, in the present embodiment, the recessed grooves 585 (see FIG. 7A) that hollow toward the opposite side to the side on which the cut area CA is located do not exist at the parts, i.e., edges, that are brought into contact with the treatment target Ap and can contribute to cutting of the treatment target Ap. That is, at the edges 96, the recessed grooves 585 (see FIG. 7A) do not exist in the direction from the surface, i.e., cut area CA, actually cut in the state in which the treatment portion 44 is in contact with the bone B of the treatment target Ap toward the longitudinal axis C of the treatment portion 44.

As described hereinbefore, when the treatment portion 44 of the ultrasonic probe 26 of the present embodiment is used, the cut area CA in which the project-shaped parts CA1 do not exist is formed. When the cut area CA is formed as such a surface, a trouble that articular surfaces of bones get caught on each other, and so forth, can be suppressed. That is, possibly not the project-shaped part CA1 but a recessed part, i.e., linear part CA2, is formed in the cut area CA. The recessed part, i.e., linear part CA2, gives influence less readily when articular surfaces of bones are moved against each other, differently from the project-shaped part CA1.

Furthermore, with the treatment portion 44 like, for example, a regular dodecahedron according to the present embodiment, it is hard that the project-shaped part CA1 be formed in the curved surface CA0 as illustrated in FIG. 7B both when the cut area CA is made through two-dimensionally moving the longitudinal axis C of the treatment portion 44 as illustrated in FIG. 4A and when the cut area CA is made through three-dimensionally moving the longitudinal axis C of the treatment portion 44 as illustrated in FIG. 5A. For this reason, when a treatment is carried out by using the probe 26 having the treatment portion 44 according to the present embodiment, a trouble that articular surfaces of the bones B get caught on each other, and so forth, can be suppressed. This allows the operator who holds the probe 26 having the treatment portion 44 according to the present embodiment to carry out an appropriate treatment with which a trouble that articular surfaces of the bones B get caught on each other, and so forth, can be suppressed in cutting of a bone or the like by use of action of ultrasonic vibration by moving the treatment portion 44 in movement directions with which the longitudinal axis C of the treatment portion 44 moves on a two-dimensional or appropriate three-dimensional locus, that is, moving the treatment portion 44 omnidirectionally.

Therefore, according to the present embodiment, it is possible to provide the ultrasonic probe 26, the ultrasonic treatment instrument 12, and the ultrasonic treatment assembly 18 that can prevent the occurrence of a trouble that an articular surface of a bone including a cut area gets caught on an articular surface of an opposed bone when the articular surface of the opposed bone moves, and so forth, when a treatment such as a cutting treatment is carried out.

Although the example in which the treatment portion 44 according to the present embodiment has one pentagonal face of a regular dodecahedron as the distal surface is described, an appropriate vertex of a pentagon may be disposed as the distal end.

Modification Example

Next, a modification example of the second embodiment will be described by using FIG. 13.

The treatment portion 44 according to the present embodiment is formed through combining plural planes as a polyhedron. In particular, the treatment portion 44 according to the present embodiment is formed as a regular icosahedron, for example. The regular icosahedron is a projected polyhedron obtained by surrounding a space by twenty triangles. The treatment portion 44 has a vertex 102a common to five triangles as the distal end, for example. In the treatment portion 44, a position closer to the center of gravity G than the vertex on the opposite side to the distal end 102a of the treatment portion 44 across the center of gravity G of the treatment portion 44 corresponds with the distal end of the probe main portion 42.

The treatment portion 44 has the distal treatment portion 44a, the proximal treatment portion 44b, and an intermediate treatment portion 44c. The distal treatment portion 44a is formed of edges and faces based on the vertex 102a and vertices 102b, 102c, 102d, 102e, and 102f each linked to the vertex 102a. The proximal treatment portion 44b is formed of edges and faces based on a distal surface 70a of the probe main portion 42 and vertices 102g, 102h, 102i, 102j, and 102k each linked to the distal surface 70a. When the intermediate treatment portion 44c is viewed from the distal side along the longitudinal axis C, a regular decagon is recognized due to the shift of the vertices 102b, 102c, 102d, 102e, and 102f from the vertices 102g, 102h, 102i, 102j, and 102k around the longitudinal axis C. At this time, when the treatment portion 44 is two-dimensionally moved in the direction D1 or the direction D2 as illustrated in FIG. 4A, the finished surface of the cut area CA like that illustrated in FIG. 12B or FIG. 12C is formed, for example.

That is, when the treatment portion 44 according to the present modification example is used, only a recessed surface that hollows relative to the pair of outer rims Ea and Eb or the pair of outer rims Ec and Ed of the cut area CA is continuously formed. For this reason, a project-shaped surface is not formed in the cut area CA.

The part that can contribute to cutting of the treatment target Ap, i.e., edge, in the treatment portion 44 according to the present modification example continuously forms, in the cut area CA, only a recessed surface that hollows relative to the pair of outer rims of the cut area CA along the movement directions D3 and D4 similarly to the case illustrated in FIG. 5B. That is, a project-shaped surface is not formed in the cut area CA.

Although the example in which the vertex of five triangles of the regular icosahedron is disposed as the distal end is described in the present modification example, one triangular face may be disposed as the distal surface.

Figure 13:
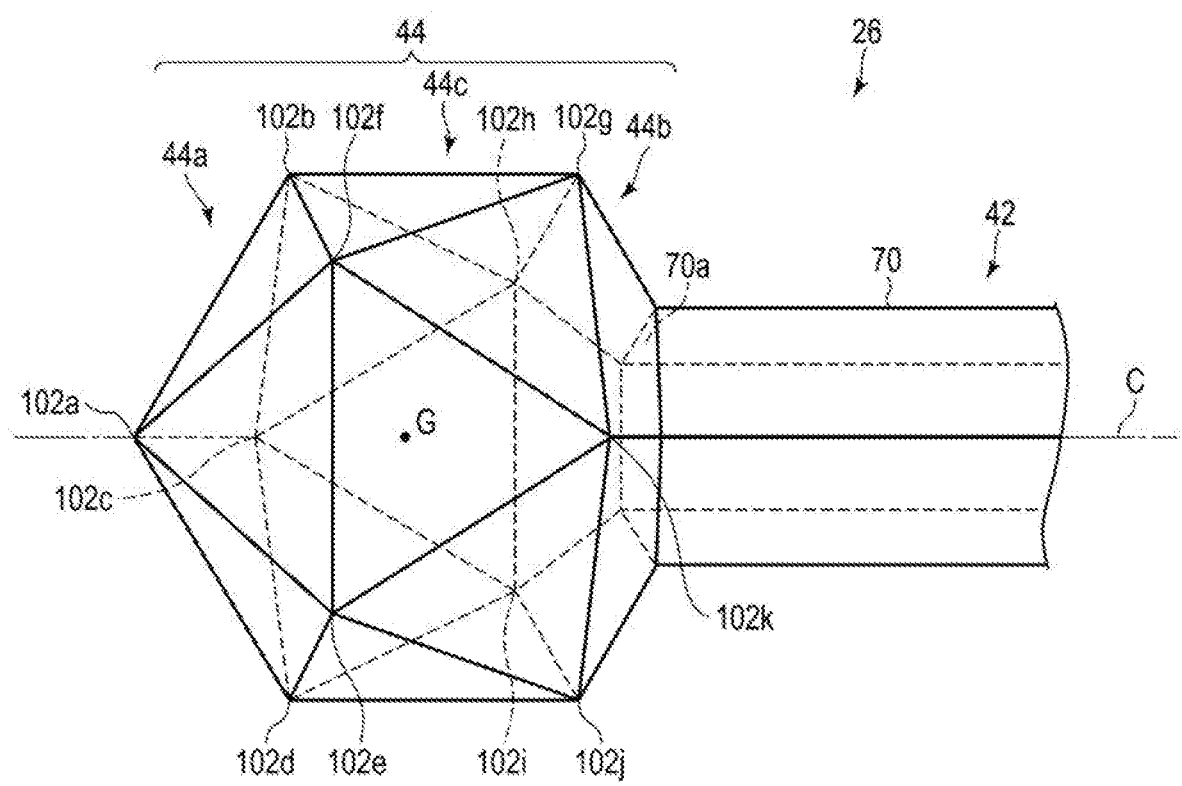
FIG. 13 is a schematic diagram in which a treatment portion of an ultrasonic probe and the distal portion of a probe main portion according to a first modification example of the second embodiment are enlarged.

Furthermore, although the examples in which planes with the same shape are combined are described in FIG. 12A and FIG. 13, the treatment portion 44 having a shape of an icosidodecahedron may be formed through combining planes of regular pentagons and regular triangles, for example. Moreover, the treatment portion 44 having a shape of a rhombitruncated icosidodecahedron may be formed through combining squares, regular hexagons, and regular decagons. As described hereinbefore, forming the treatment portion 44 through combining planes of different polygons is permitted.

Besides, by using the treatment portion 44 that is formed of a larger number of planes and curved surfaces and has an outer shape like a mirror ball, for example, generation of the linear part CA2 can be suppressed compared with the case of using the treatment portion 44 of the regular dodecahedron or the regular icosahedron described in the present embodiment.

Although the description is specifically made thus far about several embodiments with reference to the drawings, the disclosed technology is not limited to the embodiments described hereinbefore and includes all implementations carried out in such a range as not to depart from the gist thereof.

In sum, the disclosed technology is directed to an ultrasonic probe comprises a probe main portion configured to transmit ultrasonic vibration generated by an ultrasonic transducer. A treatment portion is configured to be disposed on a distal side of the probe main portion along a longitudinal axis of the probe main portion. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when being viewed from a distal side of the treatment portion along the longitudinal axis and one or more surfaces formed into a staircase shape when being viewed from a side opposed to the distal side of the treatment portion with respect to the longitudinal axis. The second direction surfaces further includes a plurality of surfaces formed into a staircase shape toward the distal side and one or more surfaces formed into a staircase shape toward the side opposed to the distal side when the treatment portion is viewed from a direction orthogonal to the longitudinal axis.

The first direction surfaces and the second direction surfaces are seamlessly continuous at an outer circumference of the treatment portion. The first direction surfaces or the second direction surfaces are disposed on an outer circumferential surface of a virtual three-dimensional object with a substantially spherical shape or a substantially ellipsoidal shape or in a vicinity of the outer circumferential surface. The treatment portion is formed substantially symmetrically with respect to the longitudinal axis. The treatment portion has one edge or a plurality of edges formed by the first direction surfaces and the second direction surfaces. The plurality of edges are made so as to get further away from the longitudinal axis as a position of the edge is shifted from the distal side toward a proximal side along the longitudinal axis. The treatment portion has one edge or a plurality of edges formed by the first direction surfaces and the second direction surfaces. The plurality of edges are made to get further away from the longitudinal axis as a position of the edge is shifted from a proximal side toward the distal side along the longitudinal axis. The treatment portion has one edge or a plurality of edges formed by the first direction surfaces and the second direction surfaces, and the plurality of edges are each formed into a ring shape.

Another aspect of the disclosed technology is directed to an ultrasonic treatment instrument incorporating an ultrasonic probe comprises a probe main portion configured to transmit ultrasonic vibration generated by an ultrasonic transducer. A treatment portion is configured to be disposed on a distal side of the probe main portion along a longitudinal axis of the probe main portion. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when is viewed from a distal side of the treatment portion along the longitudinal axis and one or more surfaces formed into a staircase shape when is viewed from a side opposed to the distal side of the treatment portion with respect to the longitudinal axis. The second direction surfaces further includes a plurality of surfaces formed into a staircase shape toward the distal side and one or more surfaces formed into a staircase shape toward the side opposed to the distal side when the treatment portion is viewed from a direction orthogonal to the longitudinal axis. A cylindrical sheath covers the probe main portion of the ultrasonic probe. A housing supports a proximal portion of the sheath and connects a proximal portion of the probe main portion to the ultrasonic transducer to a state in which the ultrasonic vibration is transmitted to the probe main portion generated by the ultrasonic transducer.

A further aspect of the disclosed technology is directed to an ultrasonic treatment assembly incorporating an ultrasonic probe that comprises a probe main portion configured to transmit ultrasonic vibration generated by an ultrasonic transducer. A treatment portion is configured to be disposed on a distal side of the probe main portion along a longitudinal axis of the probe main portion. The treatment portion includes first direction surfaces disposed in a first direction intersecting the longitudinal axis and second direction surfaces that are adjacent to the first direction surfaces and are disposed in a second direction different from the first direction surfaces. The first direction surfaces further includes a plurality of surfaces formed into a staircase shape when is viewed from a distal side of the treatment portion along the longitudinal axis and one or more surfaces formed into a staircase shape when is viewed from a side opposed to the distal side of the treatment portion with respect to the longitudinal axis. The second direction surfaces further includes a plurality of surfaces formed into a staircase shape toward the distal side and one or more surfaces formed into a staircase shape toward the side opposed to the distal side when the treatment portion is viewed from a direction orthogonal to the longitudinal axis. A cylindrical sheath covers the probe main portion of the ultrasonic probe. A housing supports a proximal portion of the sheath and connects a proximal portion of the probe main portion to the ultrasonic transducer to a state in which the ultrasonic vibration is transmitted to the probe main portion generated by the ultrasonic transducer. A transducer unit is defined by the ultrasonic transducer that is connected to the proximal portion of the probe main portion along the longitudinal axis and transmits the ultrasonic vibration to a proximal end of the probe main portion of the treatment portion.

Yet, a further aspect of the disclosed technology is directed to a method of operating an ultrasonic probe that includes a treatment portion having first direction surfaces disposed in a staircase manner in a direction intersecting a longitudinal axis, second direction surfaces disposed in a staircase manner in a direction different from the first direction surfaces, and one edge or a plurality of edges formed by the first direction surfaces and the second direction surfaces. The method comprises contacting a treatment target with the treatment portion; applying ultrasonic vibration energy by using the treatment portion while moving the treatment portion along the longitudinal axis of the ultrasonic probe with respect to the treatment target; and cutting the treatment target therethrough by maneuvering the treatment portion along of the longitudinal axis of the ultrasonic probe.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An ultrasonic probe comprising:
a probe main portion configured to transmit ultrasonic vibration generated by an ultrasonic transducer; and
a treatment portion disposed on a distal side of the probe main portion along a longitudinal axis of the probe main portion,
wherein:
the treatment portion includes first direction surfaces extending in a first direction intersecting the longitudinal axis and second direction surfaces that are adjacent to the first direction surfaces and extend in a second direction different from the first direction surfaces,
the first direction surfaces and the second direction surfaces are arranged so as to form a staircase shape when viewed from a distal side of the treatment portion along the longitudinal axis and when viewed from a proximal side opposed to the distal side of the treatment portion with respect to the longitudinal axis,
the second direction surfaces include:
a distal-most second direction surface that is distal of all other second direction surfaces along the longitudinal axis,
a proximal-most second direction surface that is proximal of all other second direction surfaces along the longitudinal axis,
an intermediate second direction surface that is: (i) disposed in between the distal-most second direction surface and the proximal-most second direction surface along the longitudinal axis, and (ii) farthest from the longitudinal axis among all of the second direction surfaces, and
a further second direction surface that is disposed in between the distal-most second direction surface and the intermediate second direction surface along the longitudinal axis,
a distance between the proximal-most second direction surface and the longitudinal axis is: (i) larger than a distance between the distal-most second direction surface and the longitudinal axis, and (ii) smaller than a distance between the intermediate second direction surface and the longitudinal axis,
the first direction surfaces include at least:
a distal-most first direction surface that is distal of all other first direction surfaces along the longitudinal axis, and faces in a distal direction along the longitudinal axis,
a first intermediate first direction surface that is proximal of the distal-most first direction surface, and faces in the distal direction,
a second intermediate first direction surface that is proximal of the first intermediate first direction surface, and faces in the distal direction, and
a proximal-most first direction surface that is proximal of all other first direction surfaces along the longitudinal axis, and faces in a proximal direction along the longitudinal axis,
the distal-most second direction surface extends directly from an outer edge of the distal-most first direction surface to the first intermediate first direction surface in a direction parallel to the longitudinal axis,
the further second direction surface extends directly from an outer edge of the first intermediate first direction surface to the second intermediate first direction surface in the direction parallel to the longitudinal axis, and
an entirety of the distal-most second direction surface is disposed closer to the longitudinal axis than an entirety of the further second direction surface is to the longitudinal axis of the probe main portion.

2. The ultrasonic probe of claim 1, wherein the first direction surfaces and the second direction surfaces are seamlessly continuous at an outer circumference of the treatment portion.

3. The ultrasonic probe of claim 1, wherein the first direction surfaces or the second direction surfaces are disposed on an outer circumferential surface of a virtual three-dimensional object with a substantially spherical shape or a substantially ellipsoidal shape or in a vicinity of the outer circumferential surface.

4. The ultrasonic probe of claim 1, wherein the treatment portion is formed substantially symmetrically with respect to the longitudinal axis.

5. The ultrasonic probe of claim 1, wherein the treatment portion includes a plurality of edges that are formed by the first direction surfaces and the second direction surfaces, and are arranged along the longitudinal axis from the the distal side of the treatment portion toward the proximal side of the treatment portion at increasing distances from the longitudinal axis.

6. The ultrasonic probe of claim 1, wherein the treatment portion includes a plurality of edges that are formed by the first direction surfaces and the second direction surfaces, and are arranged along the longitudinal axis from the proximal side of the treatment portion toward the distal side of the treatment portion at increasing distances from the longitudinal axis.

7. The ultrasonic probe of claim 1, wherein the treatment portion includes a plurality of edges formed by the first direction surfaces and the second direction surfaces, and the plurality of edges are each formed into a ring shape.

8. An ultrasonic treatment instrument incorporating an ultrasonic probe comprising:
a probe main portion configured to transmit ultrasonic vibration generated by an ultrasonic transducer; and
a treatment portion disposed on a distal side of the probe main portion along a longitudinal axis of the probe main portion,
wherein:
the treatment portion includes first direction surfaces extending in a first direction intersecting the longitudinal axis and second direction surfaces that are adjacent to the first direction surfaces and extend in a second direction different from the first direction surfaces,
the first direction surfaces and the second direction surfaces are arranged so as to form a staircase shape when viewed from a distal side of the treatment portion along the longitudinal axis and when viewed from a proximal side opposed to the distal side of the treatment portion with respect to the longitudinal axis,
the second direction surfaces include:
a distal-most second direction surface that is distal of all other second direction surfaces along the longitudinal axis,
a proximal-most second direction surface that is proximal of all other second direction surfaces along the longitudinal axis, an intermediate second direction surface that is: (i) disposed in between the distal-most second direction surface and the proximal-most second direction surface along the longitudinal axis, and (ii) farthest from the longitudinal axis among all of the second direction surfaces, and a further second direction surface that is disposed in between the distal-most second direction surface and the intermediate second direction surface along the longitudinal axis, a distance between the proximal-most second direction surface and the longitudinal axis is: (i) larger than a distance between the distal-most second direction surface and the longitudinal axis, and (ii) smaller than a distance between the intermediate second direction surface and the longitudinal axis, the first direction surfaces include at least:
- a distal-most first direction surface that is distal of all other first direction surfaces along the longitudinal axis, and faces in a distal direction along the longitudinal axis,
- a first intermediate first direction surface that is proximal of the distal-most first direction surface, and faces in the distal direction,
- a second intermediate first direction surface that is proximal of the first intermediate first direction surface, and faces in the distal direction, and
- a proximal-most first direction surface that is proximal of all other first direction surfaces along the longitudinal axis, and faces in a proximal direction along the longitudinal axis, the distal-most second direction surface extends directly from an outer edge of the distal-most first direction surface to the first intermediate first direction surface in a direction parallel to the longitudinal axis, the further second direction surface extends directly from an outer edge of the first intermediate first direction surface to the second intermediate first direction surface in the direction parallel to the longitudinal axis, an entirety of the distal-most second direction surface is disposed closer to the longitudinal axis than an entirety of the further second direction surface is to the longitudinal axis of the probe main portion, a cylindrical sheath covers the probe main portion of the ultrasonic probe, and a housing supports a proximal portion of the cylindrical sheath and connects a proximal portion of the probe main portion to the ultrasonic transducer to a state in which the ultrasonic vibration is transmitted to the probe main portion generated by the ultrasonic transducer.

9. An ultrasonic treatment assembly incorporating an ultrasonic probe comprising:

a probe main portion configured to transmit ultrasonic vibration generated by an ultrasonic transducer; and a treatment portion disposed on a distal side of the probe main portion along a longitudinal axis of the probe main portion, wherein:
the treatment portion includes first direction surfaces extending in a first direction intersecting the longitudinal axis and second direction surfaces that are adjacent to the first direction surfaces and extend in a second direction different from the first direction surfaces, the first direction surfaces and the second direction surfaces are arranged so as to form a staircase shape when viewed from a distal side of the treatment portion along the longitudinal axis and when viewed from a proximal side opposed to the distal side of the treatment portion with respect to the longitudinal axis, the second direction surfaces include:
- a distal-most second direction surface that is distal of all other second direction surfaces along the longitudinal axis,
- a proximal-most second direction surface that is proximal of all other second direction surfaces along the longitudinal axis,
- an intermediate second direction surface that is: (i) disposed in between the distal-most second direction surface and the proximal-most second direction surface along the longitudinal axis, and (ii) farthest from the longitudinal axis among all of the second direction surfaces, and
- a further second direction surface that is disposed in between the distal-most second direction surface and the intermediate second direction surface along the longitudinal axis, a distance between the proximal-most second direction surface and the longitudinal axis is: (i) larger than a distance between the distal-most second direction surface and the longitudinal axis, and (ii) smaller than a distance between the intermediate second direction surface and the longitudinal axis, the first direction surfaces include at least:
- a distal-most first direction surface that is distal of all other first direction surfaces along the longitudinal axis, and faces in a distal direction along the longitudinal axis,
- a first intermediate first direction surface that is proximal of the distal-most first direction surface, and faces in the distal direction,
- a second intermediate first direction surface that is proximal of the first intermediate first direction surface, and faces in the distal direction, and
- a proximal-most first direction surface that is proximal of all other first direction surfaces along the longitudinal axis, and faces in a proximal direction along the longitudinal axis, the distal-most second direction surface extends directly from an outer edge of the distal-most first direction surface to the first intermediate first direction surface in a direction parallel to the longitudinal axis, the further second direction surface extends directly from an outer edge of the first intermediate first direction surface to the second intermediate first direction surface in the direction parallel to the longitudinal axis, and an entirety of the distal-most second direction surface is disposed closer to the longitudinal axis than an entirety of the further second direction surface is to the longitudinal axis of the probe main portion, a cylindrical sheath covers the probe main portion of the ultrasonic probe, a housing supports a proximal portion of the cylindrical sheath and connects a proximal portion of the probe main portion to the ultrasonic transducer to a state in which the ultrasonic vibration is transmitted to the probe main portion generated by the ultrasonic transducer, and a transducer unit defined by the ultrasonic transducer that is connected to the proximal portion of the probe main portion along the longitudinal axis and is configured to transmit the ultrasonic vibration to a proximal end of the probe main portion of the treatment portion.

10. A method of operating the ultrasonic probe according to claim 1, the method comprising:
   contacting a treatment target with the treatment portion;
   applying ultrasonic vibration energy by using the treatment portion while moving the treatment portion in a direction along the longitudinal axis of the ultrasonic probe with respect to the treatment target; and
   cutting the treatment target therethrough by maneuvering the treatment portion along the direction of the longitudinal axis of the ultrasonic probe.

\* \* \* \* \*